United States Patent
Nie et al.

(10) Patent No.: US 12,293,822 B2
(45) Date of Patent: *May 6, 2025

(54) AUTOMATIC ASSAY ASSESSMENT AND NORMALIZATION FOR IMAGE PROCESSING

(71) Applicant: Ventana Medical Systems, Inc., Tucson, AZ (US)

(72) Inventors: Yao Nie, Sunnyvale, CA (US); Maria V. Sainz De Cea, Chicago, IL (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/625,118

(22) Filed: Apr. 2, 2024

(65) Prior Publication Data
US 2024/0266035 A1 Aug. 8, 2024

Related U.S. Application Data

(63) Continuation of application No. 18/326,716, filed on May 31, 2023, now Pat. No. 11,990,228, which is a (Continued)

(51) Int. Cl.
*G06T 3/40* (2024.01)
*G01N 15/1433* (2024.01)
(Continued)

(52) U.S. Cl.
CPC ......... *G16H 30/40* (2018.01); *G01N 15/1433* (2024.01); *G06F 16/535* (2019.01);
(Continued)

(58) Field of Classification Search
CPC .... G06V 10/56; G06V 16/535; G06V 20/698; G06V 10/42; G16H 70/60; G16H 10/40;
(Continued)

(56) References Cited

U.S. PATENT DOCUMENTS

| | | |
|---|---|---|
| 5,650,327 A | 7/1997 | Copeland et al. |
| 5,654,200 A | 8/1997 | Copeland et al. |

(Continued)

FOREIGN PATENT DOCUMENTS

| | | |
|---|---|---|
| CN | 103679184 A | 3/2014 |
| CN | 104408717 A | 3/2015 |

(Continued)

OTHER PUBLICATIONS

U.S. Appl. No. 16/777,649, "Non-Final Office Action", Aug. 31, 2021, 7 pages.

(Continued)

*Primary Examiner* — Edward Park
(74) *Attorney, Agent, or Firm* — Kilpatrick Townsend & Stockton LLP

(57) ABSTRACT

Disclosed herein are systems and methods for of assessing stain titer levels. An exemplary method includes generating a set of field of views for the image or the region of the image, selecting field of views from the set of field of views that meet predefined criteria, creating a series of patches within each of the selected field of views, retaining patches from the series of patches that meet predefined criteria indicative of a presence of the stain for which the titer is to be estimated, deriving stain color features and stain intensity features pertaining to the stain from the retained patches, estimating a titer score for each of the retained patches based on the stain color features and the stain intensity features, and calculating a weighted average score for the titer of the stain based on the estimated titer score for each of the retained patches.

20 Claims, 16 Drawing Sheets
(2 of 16 Drawing Sheet(s) Filed in Color)

Related U.S. Application Data continuation of application No. 17/827,656, filed on May 27, 2022, now Pat. No. 11,715,557, which is a continuation of application No. 16/777,649, filed on Jan. 30, 2020, now Pat. No. 11,380,085, which is a continuation of application No. PCT/EP2018/070978, filed on Aug. 2, 2018.

(60) Provisional application No. 62/541,621, filed on Aug. 4, 2017.

(51) Int. Cl.
| | | |
|---|---|---|
| *G06F 16/535* | (2019.01) | |
| *G06F 18/214* | (2023.01) | |
| *G06V 20/69* | (2022.01) | |
| *G16H 10/40* | (2018.01) | |
| *G16H 30/40* | (2018.01) | |
| *G16H 50/20* | (2018.01) | |
| *G16H 70/60* | (2018.01) | |
| *G01N 15/10* | (2006.01) | |

(52) U.S. Cl.
CPC .............. *G06F 18/214* (2023.01); *G06T 3/40* (2013.01); *G06V 20/698* (2022.01); *G16H 10/40* (2018.01); *G16H 50/20* (2018.01); *G16H 70/60* (2018.01); *G01N 2015/1006* (2013.01)

(58) Field of Classification Search
CPC .... G16H 50/20; G16H 30/40; G01N 15/1475; G06K 9/6256; G06T 3/40
See application file for complete search history.

(56) References Cited

U.S. PATENT DOCUMENTS

| | | | |
|---|---|---|---|
| 6,296,809 | B1 | 10/2001 | Richards et al. |
| 6,352,861 | B1 | 3/2002 | Copeland et al. |
| 6,827,901 | B2 | 12/2004 | Copeland et al. |
| 6,943,029 | B2 | 9/2005 | Copeland et al. |
| 8,042,022 | B2 | 10/2011 | Ito et al. |
| 11,380,085 | B2 * | 7/2022 | Nie .................... G06F 18/214 |
| 11,715,557 | B2 | 8/2023 | Nie et al. |
| 2003/0211630 | A1 | 11/2003 | Richards et al. |
| 2004/0052685 | A1 | 3/2004 | Richards et al. |
| 2009/0074266 | A1 | 3/2009 | Pinard et al. |
| 2010/0056940 | A1 * | 3/2010 | Moorman .............. A61B 5/349 600/509 |
| 2013/0266201 | A1 | 10/2013 | Pautot |
| 2016/0300345 | A1 | 10/2016 | Yoshihara |
| 2020/0279126 | A1 * | 9/2020 | Nie .................... G06V 20/698 |

FOREIGN PATENT DOCUMENTS

| | | |
|---|---|---|
| CN | 111512383 A | 8/2020 |
| EP | 3662484 A1 | 6/2020 |
| JP | 2008309662 A | 12/2008 |
| JP | 7047059 B2 | 3/2022 |
| WO | 2011049608 A2 | 4/2011 |
| WO | 2014195193 A1 | 12/2014 |
| WO | 2015124772 A1 | 8/2015 |
| WO | 2017049226 A1 | 3/2017 |
| WO | 2019025533 A1 | 2/2019 |

OTHER PUBLICATIONS

U.S. Appl. No. 16/777,649 , "Notice of Allowance", Mar. 8, 2022, 9 pages.
U.S. Appl. No. 17/827,656 , "Corrected Notice of Allowability", Apr. 14, 2023, 2 pages.
U.S. Appl. No. 17/827,656 , "Corrected Notice of Allowability", May 4, 2023, 3 pages.
U.S. Appl. No. 17/827,656 , "Notice of Allowance", Mar. 16, 2023, 9 pages.
U.S. Appl. No. 18/326,716 , "Notice of Allowance", Feb. 28, 2024, 9 pages.
Achanta et al., "SLIC Superpixels Compared to State-of-the-Art Superpixel Methods", IEEE Transactions on Pattern Analysis and Machine Intelligence, vol. 34, No. 11, Nov. 2012, pp. 2274-2281.
Ausubel et al., "Current Protocols in Molecular Biology", Greene Publishing Associates and Wiley-Intersciences, 1987, 22 pages.
Bankman , "Handbook of Medical Imaging, Processing and Analysis", Academic Press, Chapter 2, 2000, 910 pages.
Bejnordi et al., "Stain Specific Standardization of Whole-Slide Histopathological Images", Institute of Electrical and Electronics Engineers Transactions on Medical Imaging, vol. 35, No. 2, Feb. 1, 2016, pp. 404-415.
CN Application No. 201880062455.2 , "Notice of Decision to Grant", Jun. 25, 2023, 4 pages.
CN Application No. 201880062455.2 , "Office Action", Feb. 23, 2023, 7 pages.
EP Application No. 18759553.3 , "Intention to Grant", Jul. 18, 2023, 9 pages.
EP Application No. 23208934.2 , "Extended European Search Report", Feb. 7, 2024, 10 pages.
Gavrilovic et al., "Blind Color Decomposition of Histological Images", IEEE Transactions on Medical Imaging, IEEE Service Center, vol. 32, No. 6, Jun. 11, 2013, pp. 983-994.
Gonzalez et al., "Digital Image Processing", Third Edition, Chapter 10, 2008, 5 pages.
JP Application No. 2020-505322 , "Notice of Allowance", Feb. 22, 2022, 3 pages.
JP Application No. 2020-505322 , "Office Action", Aug. 6, 2021, 4 pages.
JP Application No. 2022-045397 , "Notice of Allowance", Mar. 29, 2023, 3 pages.
JP Application No. 2023-073117 , "Office Action", Mar. 12, 2024, 7 pages.
Khan et al., "A Nonlinear Mapping Approach to Stain Normalization in Digital Histopathology Images Using Image-Specific Color Deconvolution", IEEE Transactions on Biomedical Engineering, vol. 61, No. 6, Jun. 2014, pp. 1729-1738.
Kong et al., "A Generalized Laplacian of Gaussian Filter for Blob Detection and Its Applications", IEEE Transactions on Cybernetics, vol. 43, No. 6, Dec. 2013, pp. 1719-1733.
Kothari et al., "Automatic Batch-Invariant Color Segmentation of Histological Cancer Images", IEEE International Symposium on Biomedical Imaging: From Nano to Macro, Mar. 30-Apr. 2, 2011, pp. 657-660.
Lawson et al., "Solving Least squares Problems", Prentice Hall, Chapter 23, 1974, 6 pages.
Li et al., "A Complete Color Normalization Approach to Histopathology Images Using Color Cues Computed From Saturation-Weighted Statistics", IEEE Transactions on Bio-Medical Engineering, vol. 62, No. 7, Jul. 2015, pp. 1862-1873.
Nie et al., "Quantifying Immunohistochemical Expression of Programmed Death-1 on T-Cells", Pathology Visions Conference, Oct. 23-25, 2016.
International Application No. PCT/EP2018/070978 , "International Search Report and Written Opinion", Nov. 28, 2018, 12 pages.
Ruifrok et al., "Quantification of Histochemical Staining by Color Deconvolution", Analytical and Quantitative Cytology and Histology, vol. 23, No. 4, Aug. 2001, pp. 291-299.
Sainz De Cea et al., "Single Stain Normalization for IHC Whole Slide Images", Progress in Biomedical Optics and Imaging, vol. 10581, XP060104312, Mar. 6, 2018, pp. 1058104-1-1058104-8.
Sambrook et al., "Molecular Cloning: A Laboratory Manual", Second Edition, Cold Spring Harbor Laboratory Press, 1989, 30 pages.
Van Der Laak et al., "Hue-Saturation-Density (HSD) Model for Stain Recognition in Digital Images from Transmitted Light Spectroscopy", Cytometry, vol. 39, No. 4, Jan. 1, 2000, pp. 275-284.
Yagi , "Color Standardization and Optimization in Whole Slide Imaging", Diagnostic Pathology, vol. 6, Mar. 30, 2011, pp. 1-12.

(56) References Cited

OTHER PUBLICATIONS

Zimmermann , "Spectral Imaging and Linear Unmixing in Light Microscopy", Advancement in Biochemical Engineering and Biotechnology, vol. 95, May 2005, pp. 245-265.
JP Application No. 2023-073117 , "Notice of Allowance", Aug. 29, 2024, 6 pages.
Ehteshami Bejnordi, Babak, et al.,. Stain Specific Standardization of Whole-Slide Histopathological Images, IEEE Transaction on Medical Imaging, 米国,, IEEE, Feb. 1, 2016, vol. 35 No. 2, p. 404-415, DOI: 10.1109 /TMI.2015.2476509.

* cited by examiner

AUTOMATIC ASSAY ASSESSMENT AND NORMALIZATION FOR IMAGE PROCESSING

CROSS REFERENCES TO RELATED APPLICATIONS

The present application is a continuation of U.S. application Ser. No. 18/326,716, filed on May 31, 2023, which is a continuation of U.S. application Ser. No. 17/827,656, filed on May 27, 2022, which is a continuation of U.S. application Ser. No. 16/777,649, filed Jan. 30, 2020, which is a continuation of International Application PCT/EP2018/070978, filed Aug. 2, 2018, which claims benefit and priority to U.S. Provisional Application No. 62/541,621, filed Aug. 4, 2017. Each of these applications is hereby incorporated by reference in its entirety for all purposes.

BACKGROUND OF THE DISCLOSURE

Digital pathology involves scanning of whole histopathology or cytopathology glass slides into digital images interpretable on a computer screen. These images are to be processed subsequently by an imaging algorithm or interpreted by a pathologist. In order to examine tissue sections (which are virtually transparent), tissue sections are prepared using colored histochemical stains that bind selectively to cellular components. Color-enhanced, or stained, cellular structures are used by clinicians or a computer-aided diagnosis (CAD) algorithm to identify morphological markers of a disease, and to proceed with therapy accordingly. Observing the assay enables a variety of processes, including diagnosis of disease, assessment of response to treatment, and development of new drugs to fight disease.

Immunohistochemical (IHC) slide staining can be utilized to identify proteins in cells of a tissue section and hence is widely used in the study of different types of cells, such as cancerous cells and immune cells in biological tissue. Thus, IHC staining may be used in research to understand the distribution and localization of the differentially expressed biomarkers of immune cells (such as T-cells or B-cells) in a cancerous tissue for an immune response study. For example, tumors often contain infiltrates of immune cells, which may prevent the development of tumors or favor the outgrowth of tumors.

In-situ hybridization (ISH) can be used to look for the presence of a genetic abnormality or condition such as amplification of cancer causing genes specifically in cells that, when viewed under a microscope, morphologically appear to be malignant. In situ hybridization (ISH) employs labeled DNA or RNA probe molecules that are anti-sense to a target gene sequence or transcript to detect or localize targeted nucleic acid target genes within a cell or tissue sample. ISH is performed by exposing a cell or tissue sample immobilized on a glass slide to a labeled nucleic acid probe which is capable of specifically hybridizing to a given target gene in the cell or tissue sample. Several target genes can be simultaneously analyzed by exposing a cell or tissue sample to a plurality of nucleic acid probes that have been labeled with a plurality of different nucleic acid tags. By utilizing labels having different emission wavelengths, simultaneous multicolored analysis may be performed in a single step on a single target cell or tissue sample. For example, INFORM HER2 Dual ISH DNA Probe Cocktail Assay from Ventana Medical Systems, Inc., is intended to determine HER2 gene status by enumeration of the ratio of the HER2 gene to Chromosome 17. The HER2 and Chromosome 17 probes are detected using a two color chromogenic ISH in formalin-fixed, paraffin-embedded human breast cancer tissue specimens.

BRIEF SUMMARY OF THE DISCLOSURE

The present disclosure relates to automated systems and methods for assessing the titer of a stain within an image of a biological sample, and normalizing the titer of that stain to a titer of the same stain in a template image.

Even though most digital pathology imaging algorithms are designed to function at a certain staining concentration, the actual slides to be processed may have a wide range of variation in their hematoxylin concentration or titer levels. Without wishing to be bound by any particular theory, it is believed that such stain color and intensity variations are believed to make the hematoxylin stain in the slides either too dark or too faint and thus may introduce errors in image processing algorithms that are not designed to consider such abrupt variations in stain titer. Indeed, processing algorithms are usually tuned to work within a predefined staining concertation range; and if the concentration falls outside this range, the algorithm may fail. By using the disclosed image normalization systems and methods, the concentration (or titer) within an image may be adjusted to fall within any image processing algorithm's predefined staining concentration range. Accordingly, the disclosed systems and methods for automated stain normalization allow for a reduction in stain color and intensity variations. In addition, the automated systems and methods disclosed herein enable enhanced downstream processing of acquired images, e.g. for scoring of a biological sample or quantification of features within a histology image.

While it is possible to normalize all stains in an acquired image, it is often not desirable to do so since the intensity of certain stains may relate to specific biological indications. For example, as a target for cancer immunotherapy, programmed death-1 (PD-1) is expressed on T-cells and functions as an inhibitory receptor that down regulates the immune system. The expression level of PD-1 can be characterized by the DAB stain intensity; therefore, normalization of DAB is not desired as it is believed it may distort the PD-1 expression level information in the tissue sample. In addition, there may exist situations where a stain is always co-localized with the counter stain that marks the nucleus, e.g. estrogen receptor (ER). In such case, DAB may appear in the mixture with the counter stain hematoxylin (HTX), therefore it is infeasible to extract pure DAB color distribution for normalization. Applicants have discovered that hematoxylin, which marks the nucleus of a cell, allows for robust normalization across different slides. Applicants submit that the systems and methods described herein allow for the normalization of pure hematoxylin stain as well as hematoxylin stain co-localized with other stains, which has not been addressed before.

In one aspect of the present disclosure is a method of normalizing a titer of a first stain within a query image to a titer of the first stain in a template image, the query image of a biological sample stained with at least the first stain, comprising: (i) deriving chromatic and density distribution coordinates in the query image within a color model that includes a density component; (ii) aligning the derived chromatic distributions coordinates in the query image with template image chromatic distribution coordinates to provide transformed chromatic distribution coordinates; (iii) scaling the derived density distribution coordinates in the query image with template image density distribution coordinates to provide transformed density distribution coordinates; and (iv) reconstructing an RGB image by inversely transforming the query image within the color model that includes the density component using weighted transformed chromatic and density distribution coordinates; wherein the aligning and scaling utilize predetermined parameter values specific for an estimated titer level of the query image. Without wishing to be bound by any particular theory, it is believed that the use of predetermined parameter values or a look-up table of alignment and scaling parameters allows for the robust identification of normalization parameters, such as when there is an insufficient number of pure stain pixels to derive reliable stain color or intensity statistics. In some embodiments, the color model that includes a density component is an HSD color model.

In some embodiments, the predetermined parameter values are derived mean, angle, and scaling parameters determined at a known first stain titer level. In some embodiments, the predetermined parameter values are stored in a database, the database comprising parameter values for at least the first stain at a plurality of titer levels, and the estimated first stain titer level in the query image is matched to one of the plurality of titer levels such that the best parameter values for performing the alignment and scaling are selected. In some embodiments, the first stain is hematoxylin, and the predetermined parameter values correspond to an estimated hematoxylin titer level within the query image. In some embodiments, the estimated titer level is determined prior to normalization. In some embodiments, the estimated titer level is determined during normalization, e.g. after transforming the RGB query image to the color model that includes a density component (e.g. HSD color model), but prior to deriving transformed coordinates for each pixel.

In some embodiments, the estimated titer level of the query image is determined by computing a weighted average (or mode) titer score for the query image based on derived first stain color and intensity features. In some embodiments, the weighted average score is computed by (a) deriving a plurality of first stain image features from each of a series of patches in the query image, and (b) classifying the plurality of derived image features from each of the image patches using a trained titer-identification classifier. In some embodiments, the titer-identification classifier is a multi-class classifier trained on first stain color and intensity features derived from standardized samples using first stain titer levels as class labels. In some embodiments, the series of patches are derived by (a) extracting a predefined number of FOVs from the query image (e.g. 50 FOVs); (b) computing a set of patches for each of the extracted FOVs; and (c) retaining those patches from the set of patches for each extracted FOV that meet threshold patch criteria. In some embodiments, the first stain is hematoxylin and the criteria include: (i) greater than 70% of the pixels in the patch must have hematoxylin signal (obtained from color deconvolution) higher than 0; (b) greater than 50% of the pixels must have some staining; and (c) greater than one third of the pixels have to be arranged in a "cell-like" structure as determined by difference of Gaussian filtering.

In some embodiments, the weighted transformed chromatic and density distribution coordinates are derived by (i) computing probabilities that pixels in the patches are first stain pixels, i.e. pixels having the first stain; and (ii) weighting the transformed chromatic and density distribution coordinates with the computed probabilities. In some embodiments, the alignment comprises shifting and rotating the derived chromatic distribution coordinates in the query image to have a same mean and orientation as template chromatic distribution coordinates. In some embodiments, the scaling comprises transforming the derived density distribution coordinates to have the same weighted mean and weighted standard deviation as the density of the first stain pixels in the template image. In some embodiments, chromatic and density distribution coordinates are derived for each pixel in a series of patches in the query image.

In some embodiments, the method further comprises unmixing the RGB image prior to normalization and/or titer assessment. In some embodiments, the method further comprises extracting nuclear, membrane, morphological, and/or other cellular features from cells stained with at least the first stain. In some embodiments, the extracted nuclear, membrane morphological, and/or other cellular features are used to classify a cell, such as classifying the cell as being a tumor cell. In some embodiments, for color alignment during RGB reconstruction, instead of employing the original HTX color reference vector used for color deconvolution, the normalized average RGB OD vector from the pure HTX pixels in the template image is used for reconstruction.

In another aspect of the present disclosure is a method of assaying a titer of a first stain within a whole slide image of a biological sample stained with one or more stains, and normalizing the whole slide image relative to the titer of the first stain comprising: (i) computing a weighted average titer score for the whole slide image based on derived first stain image features; and (ii) normalizing the whole slide image to a template image if the computed weighted average score is not within a predefined titer range, wherein the whole slide image is normalized by (a) matching whole slide image chromatic and density distributions to template image chromatic and density distributions, wherein the chromatic and density distributions of both the whole slide and template images are derived within a color model that includes a density component, and (b) reconstructing an RGB image by inversing transforming the whole slide image within the color model that includes the density component using weighted transformation coordinates. In some embodiments, the predefined titer range is between about 3 and about 6. In some embodiments, the color model that includes a density component is an HSD color model.

In some embodiments, the weighted average score is computed by (a) deriving a plurality of first stain image features from each of a series of image patches in the whole slide image, and (b) classifying the plurality of derived image features from each of the image patches using a trained feature-identification classifier. In some embodiments, the series of image patches are derived by (a) extracting a predefined number of FOVs from the whole slide image; (b) computing a set of patches for each of the extracted FOVs; and (c) retaining those patches from the set of patches for each extracted FOV that meet threshold patch criteria. In some embodiments, first stain image features are stain color features and stain intensity features.

In some embodiments, the whole slide image chromatic and density distributions are matched to the template image chromatic and density distributions by (i) performing a transform (e.g. an HSD transform) within the image patches of the whole slide image to obtain chromatic and density distribution coordinates ($c_x$, cy, D) for all pixels in each of the image patches; (ii) shifting and rotating the obtained chromatic distribution coordinates ($c_x$, cy) in the whole slide image to have a same mean and orientation as template chromatic coordinates to provide aligned chromatic coordinates ($c_x'$, cy') for each pixel in each image patch; and (iii) scaling the obtained density distributions (D) from the whole slide image to have a same weighted mean and weighted standard deviation as template density distributions to provide scaled density distributions (D') for each pixel in each image patch. In some embodiments, the weighted transformation coordinates are derived by (i) computing probabilities that pixels in the image patches are first stain pixels; and (ii) weighting the aligned chromatic density distribution coordinates and scaled density distribution coordinates ($c_x'$, cy', D') with the computed probabilities. In some embodiments, for color alignment during RGB reconstruction, instead of employing the original HTX color reference vector used for color deconvolution, the normalized average RGB OD vector from the pure HTX pixels in the template image is used for reconstruction.

In some embodiments, the matching of the obtained chromatic and density distributions to template chromatic and density distributions utilize predetermined statistical parameters, wherein the predetermined statistical parameters chosen are particular for a titer level that approximates the weighted average titer score for the whole slide image. For example, if an estimated titer level of the first stain is 3, then the method retrieves predetermined statistical parameters from a database corresponding to the first stain at the known titer level of 3. In some embodiments, the first stain is hematoxylin. In some embodiments, the first stain is hematoxylin and the predetermined statistical parameters are used to align and scale the derived chromatic and density distribution coordinates from the whole slide image to the template image.

In another aspect of the present disclosure is an imaging system for normalizing a titer of a first stain within a query image to a titer of the first stain in a template image, the query image being of a biological sample stained with at least the first stain, the imaging system comprising: (i) an image acquisition device, (ii) one or more processors, and (iii) a memory coupled to the processor, the memory to store computer-executable instructions that, when executed by the one or more processors, cause the one or more processors to perform operations comprising: (a) deriving chromatic and density distribution coordinates for each pixel in generated patches within the query image within a color model that includes a density component; (b) transforming the derived chromatic and density distribution coordinates for each pixel in the generated patches using predetermined alignment and scaling parameter values specific for an estimated titer level of the query image to provide transformed chromatic and density distribution coordinates; and (c) reconstructing an RGB image by inversely transforming the query image within the color model that includes the density component using the transformed chromatic and density distribution coordinates weighted by pixel probability values. In some embodiments, the imaging system further comprises a staining apparatus. In some embodiments, the biological sample is stained with at least two stains. In some embodiments, the first stain is hematoxylin. In some embodiments, the color model that includes a density component is an HSD color model.

In some embodiments, the transforming of the derived chromatic and density distribution coordinates for each pixel in the generated patches comprises (a) shifting and rotating the derived chromatic distribution coordinates (cx, cy) for each pixel in the generated patches to have a same mean and orientation as template chromatic coordinates to provide transformed chromatic coordinates (cx', cy') for each pixel in the generated patches; and (b) scaling the obtained density distributions (D) for each pixel in the generated patches to have a same weighted mean and weighted standard deviation as template density distributions to provide transformed density distributions (D') for each pixel the generated patches. In some embodiments, the patches are generated by (a) extracting a predefined number of FOVs from the query image; (b) generating a set of patches for each of the extracted FOVs; and (c) retaining those patches from the set of patches for each extracted FOV that meet threshold patch criteria.

In some embodiments, the weighted transformed chromatic and density distribution coordinates are derived by (i) computing probabilities that pixels are first stain pixels; and (ii) weighting the transformed chromatic and density distribution coordinates with the computed probabilities.

In some embodiments, the alignment and scaling parameter values specific for the first stain at a plurality of titer levels are stored in the memory. In some embodiments, the estimated titer level of the query image is determined by computing a weighted average titer score for the query image based on derived first stain color and intensity features, and wherein the alignment and scaling parameters selected approximate the weighted average titer score of the query image. In some embodiments, the weighted average score is computed by (a) deriving a plurality of first stain image features from the generated patches in the query image, and (b) classifying the plurality of derived image features from each of the generated patches using a trained titer-identification classifier. In some embodiments, the titer-identification classifier is a multi-class classifier trained on first stain color and intensity features derived from standardized samples using first stain titer levels as class labels.

In another aspect of the present disclosure is a non-transitory computer-readable medium for assaying a titer of a first stain within a whole slide image of a biological sample stained with one or more stains, and normalizing the whole slide image relative to the titer of the first stain comprising: (i) computing a weighted average titer score for the whole slide image based on derived first stain image features, and (ii) normalizing the titer of the first stain whole slide image to a template image first stain titer, wherein the whole slide image is normalized by: (a) deriving chromatic and density distribution coordinates in the query image within a color model that includes a density component; (b) aligning the derived chromatic distributions coordinates in the query image with template image chromatic distribution coordinates to provide transformed chromatic distribution coordinates, wherein the alignment comprises shifting and rotating the derived chromatic distribution coordinates in the query image to have a same mean and orientation as template chromatic distribution coordinates, wherein the step of alignment utilizes predetermined alignment parameters matched to the computed weighted average titer score of the whole slide image; (c) scaling the derived density distribution coordinates in the query image with template image density distribution coordinates to provide transformed density distribution coordinates, wherein the scaling comprises transforming the derived density distribution coordinates to have the same weighted mean and weighted standard deviation as template density distribution coordinates, wherein the step of scaling utilizes predetermined scaling parameters matched to the computed weighted average titer score of the whole slide image; and (d) reconstructing an RGB image by inversely transforming the query image within the color model that includes the density component using weighted transformed chromatic and density distribution coordinates. In some embodiments, the first stain is hematoxylin. In some embodiments, the biological sample is stained with the one or more stains in an immunohistochemistry assay and/or in an in-situ hybridization assay. In some embodiments, the color model that includes a density component is an HSD color model.

In some embodiments, the first stain in the whole slide image is normalized to the template image first stain titer if the computed weighted average titer score falls outside a predetermined threshold titer score range. In some embodiments, the predetermined threshold titer score ranges from about 3 to about 6. In some embodiments, wherein the weighted average titer score for the whole slide image based on derived first stain image features is computed by (a) extracting a predefined number of FOVs from the whole slide image; (b) computing a set of patches within each of the extracted FOVs; (c) deriving a plurality of first stain color and intensity features from each patch within the set of patches; (d) classifying the plurality of derived first stain color and intensity features using a trained titer-classifier; and (e) computing a weighted average scored based on the classification results from all of the patches.

In some embodiments, the non-transitory computer-readable medium further comprises instructions for identifying a region of interest. In some embodiments, the non-transitory computer-readable medium further comprises instructions for unmixing an input image into individual channel images for each stain. In some embodiments, the non-transitory computer-readable medium further comprises instructions for deriving additional cellular or nuclear features after normalization. In some embodiments, the non-transitory computer-readable medium further comprises instructions for scoring the biological sample, the scoring specific to a particular assay in which the biological sample was stained.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a general understanding of the features of the disclosure, reference is made to the drawings. In the drawings, like reference numerals have been used throughout to identify identical elements.

DETAILED DESCRIPTION

Figure 1:
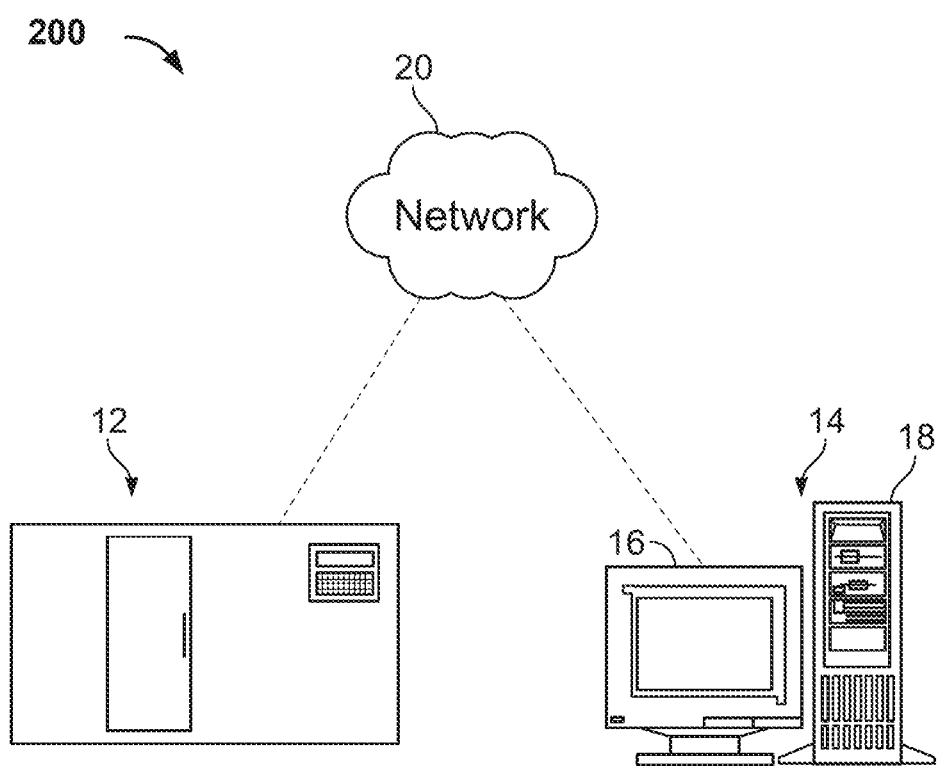
FIG. 1 illustrates a representative digital pathology system including an image acquisition device and a computer system.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the terms "biomarker" or "marker" refer to a measurable indicator of some biological state or condition. In particular, a biomarker may be a protein or peptide, e.g. a surface protein, that can be specifically stained and which is indicative of a biological feature of the cell, e.g. the cell type or the physiological state of the cell. An immune cell marker is a biomarker that is selectively indicative of a feature that relates to an immune response of a mammal. A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "blob" refers to a group of connected pixels around an identified nucleus center/seed, which represents the nucleus.

As used herein, the term "color channel" refers to a channel of an image sensor. For example, the image sensor may have three color changes, such as red (R), green (G), and blue (B).

As used herein, the term "field of view (FOV)" refers to an image portion that has a predetermined size and/or shape. In some embodiments, the FOV is a region in a digital image that is used for further manual or automated inspection and analysis. The FOV may be selected automatically or manually by analyzing some features of the digital image, e.g. by evaluating intensity values of the pixels of the digital image.

As used herein, the term "image data" as understood herein encompasses raw image data acquired from the biological tissue sample, such as by means of an optical sensor or sensor array, or pre-processed image data. In particular, the image data may comprise a pixel matrix. As used herein, the term "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection). A "mask" as used herein is a derivative of a digital image wherein each pixel in the mask is represented as a binary value, e.g. "1" or "0" (or "true" or "false"). By overlaying a digital image with said mask, all pixels of the digital image mapped to a mask pixel of a particular one of the binary values are hidden, removed or otherwise ignored or filtered out in further processing steps applied on the digital image. For example, a mask can be generated from an original digital image by assigning all pixels of the original image with an intensity value above a threshold to true and otherwise false, thereby creating a mask that will filter out all pixels overlaid by a "false" masked pixel.

A "multi-channel image" as understood herein encompasses a digital image obtained from a biological tissue sample in which different biological structures, such as nuclei and tissue structures, are simultaneously stained with specific fluorescent dyes, quantum dots, chromogens, etc., each of which fluoresces or are otherwise detectable in a different spectral band thus constituting one of the channels of the multi-channel image.

As used therein, the term "RGB color space" refers to any additive color space based on the red-green-blue (RGB) color model. A particular RGB color space is defined by the three chromaticities of the red, green, and blue additive primaries, and can produce any chromaticity that is the triangle defined by those primary colors. The complete specification of an RGB color space also requires a white point chromaticity and a gamma correction curve.

As used herein, a "template image" refers to an image with known characteristics used as a reference. The staining of this image has been determined to be appropriate for subsequent analysis, with the goal to make the rest of the images similar to this one.

As used herein, the term "titer" refers to a concentration or amount of a stain within a sample. In general, the titer level values range from about 1 to about 9; where 1 represents the lowest staining concentration, and 9 the highest staining concentration. There are a number of physical processes related to the titer like staining time, concentration, etc.

As used herein, the term "unmixed image" encompasses a grey-value or scalar image obtained for one channel of a multi-channel image. By unmixing a multi-channel image one unmixed image per channel is obtained.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Overview

Performance of image analysis algorithms in digital pathology whole slide images (WSI) may be hampered by stain variations cross images. To overcome such difficulties, many stain normalization methods have been proposed where normalization is applied to all the stains in the image. However, for immunohistochemistry (IHC) images, there exist situations where not all the stains in the images are desired or feasible to be normalized, especially when the stain variations relate to certain biological indications. In contrast, the counter stain, usually hematoxylin (HTX), is always desired to be consistent cross images for robust nuclei detection. In this work, a framework is disclosed to normalize the HTX stain in an IHC WSI through alignment to a template IHC WSI. For this purpose, the Hue-Saturation-Density (HSD) model is utilized and the chromatic components distribution of the image is aligned to the template. Then the density component is then shifted and scaled to match the template. In order to retain the non-HTX stain, the pixels which have pure HTX stain are differentiated from those which are mixture of HTX and non-HTX stains, and a different normalization strategy is applied accordingly (see Example 3).

Figure 11:
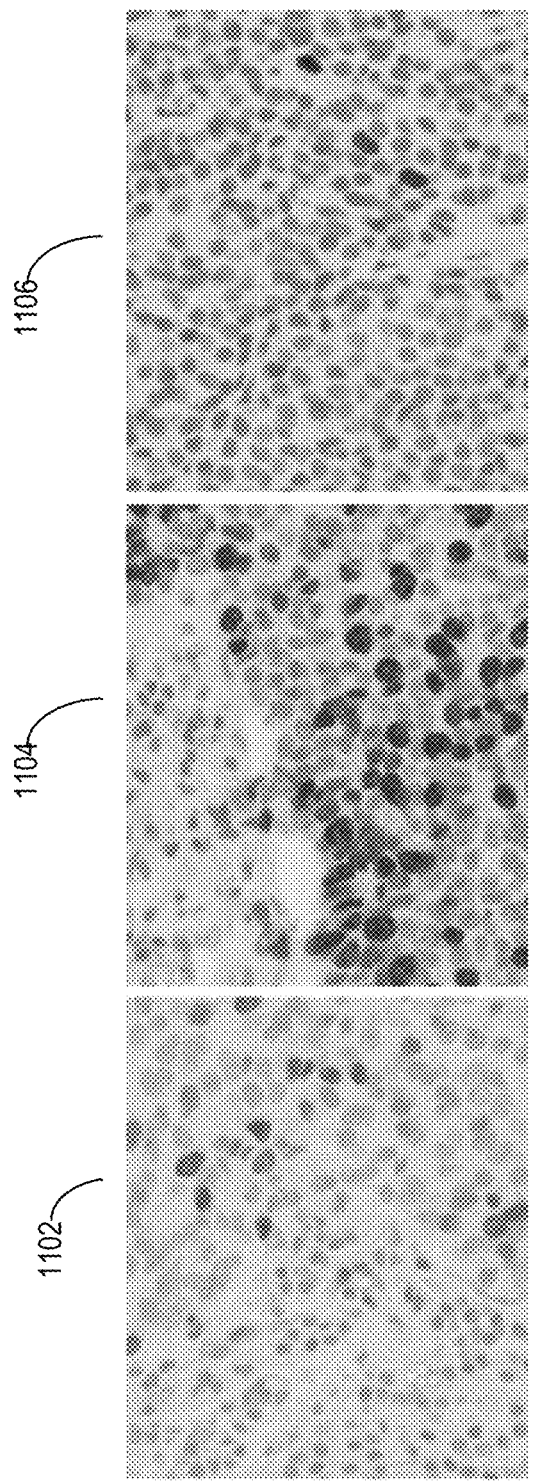
FIG. 11 illustrates estrogen receptor (ER) stained breast cancer images with different hematoxylin stains. The slides are from three different clinical labs and scanned at 20× magnification level.

Applicants have developed a preprocessing system and method that estimates whether a slide is in a desired titer range for processing. The system and method also function to align a stains' titer from a query image with the stain's titer in a template image. Applicants submit that the systems and methods described herein may be used to solve the inconsistencies among HTX staining due to pre-analytical conditions. For example, and as illustrated in FIG. 11, three ER stained breast cancer images 1102, 1104, and 1106 from three clinical labs present different HTX stain hues and intensities. It is challenging for an image processing algorithm to have consistent sensitivity for negative tumor cell identification across such images.

To overcome this, the systems and methods described herein employ a preprocessing framework to only normalize the HTX stain to a given template WSI. The proposed framework performs normalization through coordinate alignment in a color module which incorporates a density component (e.g. the Hue-Saturation-Density (HSD) color space). While the present disclosure may refer to an HSD transform, the skilled artisan will appreciate that any other suitable color space transformation may be utilized (now know or later discovered), provided that the color space incorporates density information, e.g. a density component that is linearly related to an amount of stain. In some embodiments, the color module incorporating a density component permits the derivation of density coordinates, the density coordinates (or density information) being linearly related to an amount of stain. In some embodiments, the color module incorporating a density component permits the derivation of chromatic coordinates (or chromatic information) being independent of the amount of stain.

Customized HTX pixel selection for reliable color distribution derivation and special handling for stain mixture pixels are developed to meet the single stain normalization needs of IHC image analysis. To quantify the effects of this pre-processing step on an imaging algorithm, Applicants demonstrate the results of an IHC stained cell detection algorithm for the images with and without normalization, demonstrating that the proposed method yields a more consistent detection performance among different HTX concentration levels.

A digital pathology system 200 for imaging and analyzing specimens is illustrated in FIG. 1. The digital pathology system 200 may comprise an imaging apparatus 12 (e.g. an apparatus having means for scanning a specimen-bearing microscope slide) and a computer 14, whereby the imaging apparatus 12 and computer may be communicatively coupled together (e.g. directly, or indirectly over a network 20). The computer system 14 can include a desktop computer, a laptop computer, a tablet, or the like, digital electronic circuitry, firmware, hardware, memory 602, a computer storage medium, a computer program or set of instructions (e.g. where the program is stored within the memory or storage medium), a processor (including a programmed processor), and/or the like. The computing system 14 illustrated in FIG. 1 may comprise a computer with a display device 16 and an enclosure 18. The computer system can store digital images in binary form (locally, such as in a memory, on a server, or another network connected device). The digital images can also be divided into a matrix of pixels. The pixels can include a digital value of one or more bits, defined by the bit depth. The skilled artisan will appreciate that other computer devices or systems may be utilized and that the computer systems described herein may be communicatively coupled to additional components, e.g. specimen analyzers, microscopes, other imaging systems, automated slide preparation equipment, etc. Some of these additional components and the various computers, networks, etc. that may be utilized are described further herein.

In general, the imaging apparatus 12 (or other image source including pre-scanned images stored in a memory) can include, without limitation, one or more image capture devices. Image capture devices can include, without limitation, a camera (e.g., an analog camera, a digital camera, etc.), optics (e.g., one or more lenses, sensor focus lens groups, microscope objectives, etc.), imaging sensors (e.g., a charge-coupled device (CCD), a complimentary metal-oxide semiconductor (CMOS) image sensor, or the like), photographic film, or the like. In digital embodiments, the image capture device can include a plurality of lenses that cooperate to prove on-the-fly focusing. An image sensor, for example, a CCD sensor can capture a digital image of the specimen. In some embodiments, the imaging apparatus 12 is a brightfield imaging system, a multispectral imaging (MSI) system or a fluorescent microscopy system. The digitized tissue data may be generated, for example, by an image scanning system, such as an iSCAN CORE by VENTANA MEDICAL SYSTEMS of Tucson, Ariz. or other suitable imaging equipment. Additional imaging devices and systems are described further herein. The skilled artisan will appreciate that the digital color image acquired by the imaging apparatus 12 is conventionally composed of elementary color pixels. Each colored pixel is coded over three digital components, each comprising the same number of bits, each component corresponding to a primary color, generally red, green or blue, also denoted by the term "RGB" components.

Figure 2:
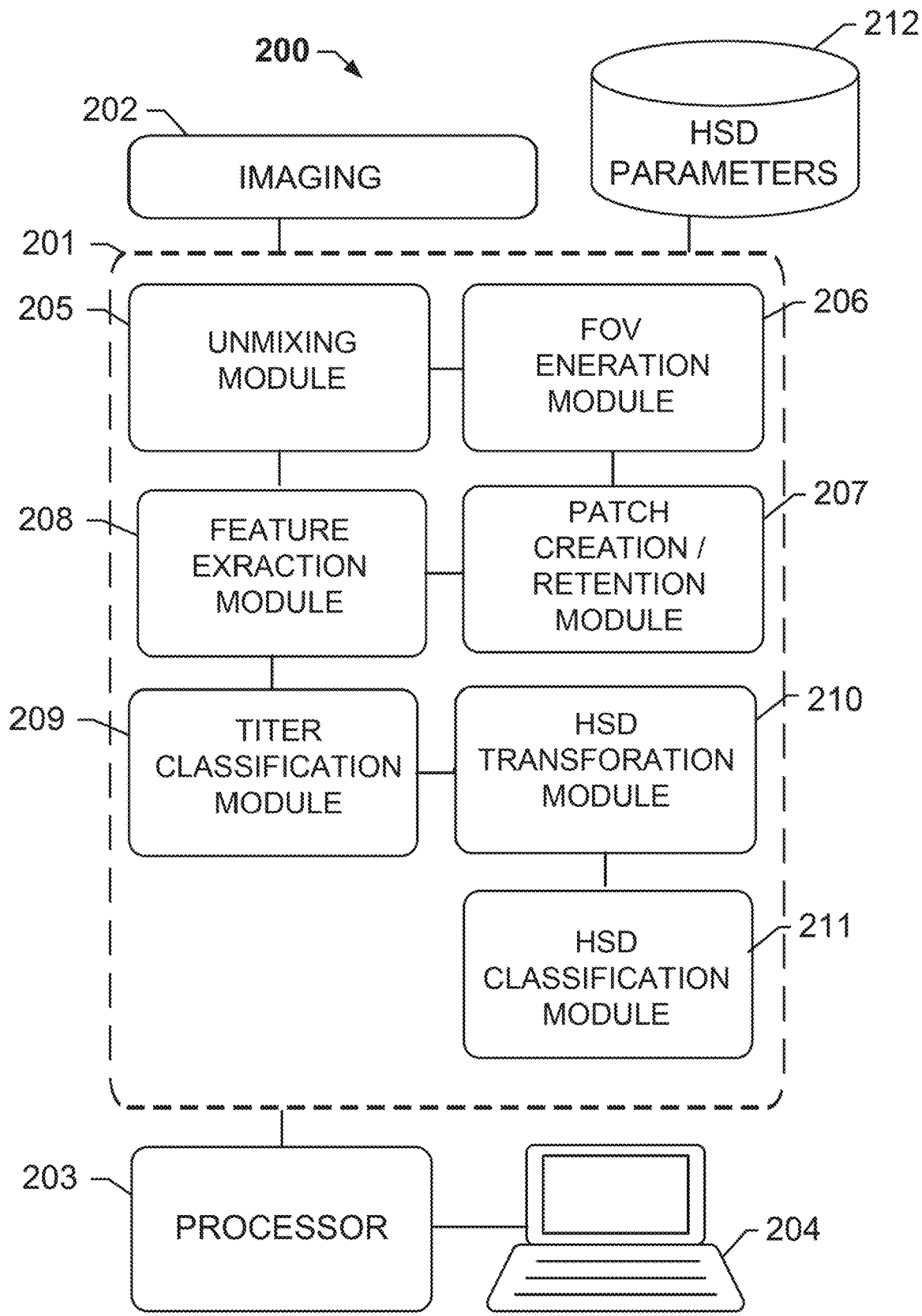
FIG. 2 sets forth various modules that can be utilized in a digital pathology system or within a digital pathology workflow.

FIG. 2 provides an overview of the various modules utilized within the presently disclosed digital pathology system. In some embodiments, the digital pathology system employs a computer device 200 or computer-implemented method having one or more processors 203 and at least one memory 201, the at least one memory 201 storing non-transitory computer-readable instructions for execution by the one or more processors to cause the one or more processors to execute instructions (or stored data) in one or more modules (e.g. modules 202, and 205 through 212). Alternatively, the instructions may be stored in a non-transitory computer-readable medium (201) or computer-usable medium. In some embodiments, a non-transitory computer-readable media 201 may comprise all computer-readable media except for a transitory, propagating signal.

Figure 3A:
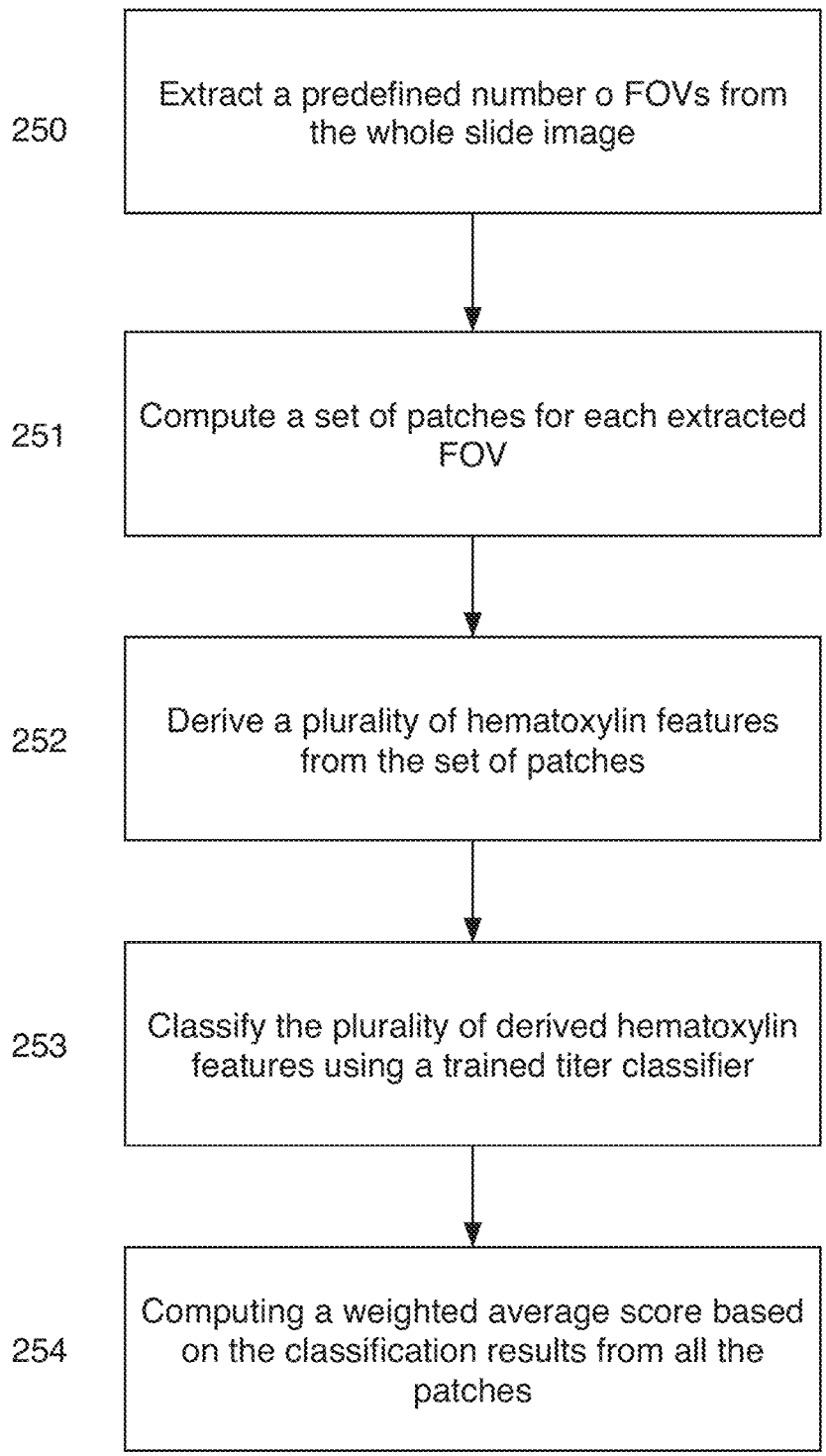
FIG. 3A provides an overview of the steps for assessing a stain titer in an image.

With reference to FIGS. 2 and 3A, the present disclosure provides a computer-implemented method of assessing or estimating a stain's titer in an acquired image, the method comprising the steps of (a) running an image acquisition module 202 to generate or receive multi-channel image data, e.g. an acquired image, or a biological sample stained with one or more stains; (b) running an unmixing module 205 to generate image channel images corresponding to one or more stain channels; (c) running a FOV generation module 206 to generate FOVs for the test image and, from amongst all the generated FOVs, select those FOV meeting pre-defined criteria (step 250); running a patch creation and retention module 207 to create a series of patches within each retained FOV, and retaining those patches meeting predefined criteria indicative of the presence of a stain whose titer is to be evaluated (step 251); running a feature extraction module 208 to derive stain color features and stain intensity features pertaining to the stain whose titer is to be estimated (step 252); and running a titer classification module 209 to classify the extracted color and stain features (step 253) and to output a weighted average score of the titer for the test image (step 254). In some embodiments, the stain is hematoxylin.

Figure 3B:
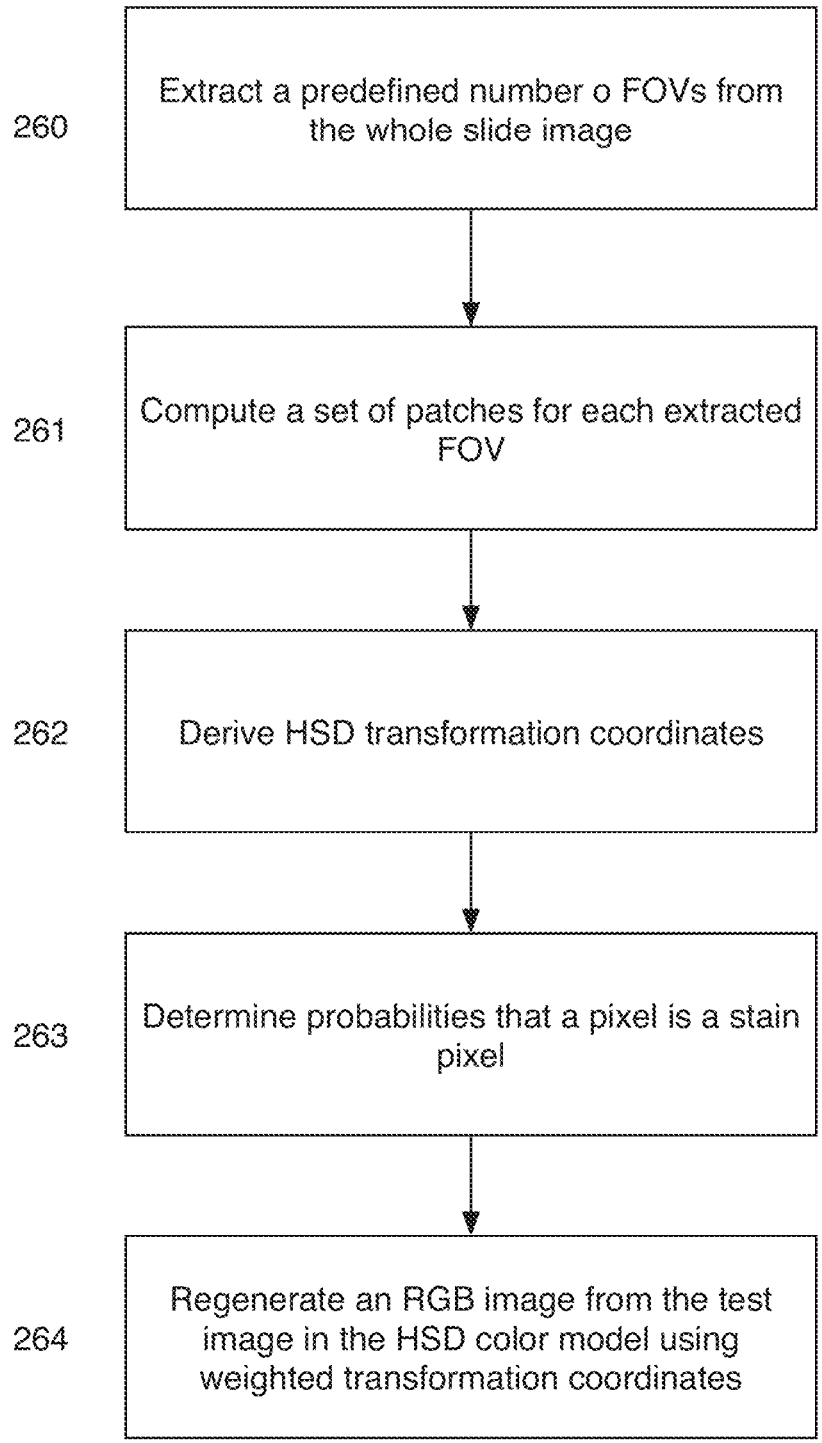
FIG. 3B provides an overview of the steps for normalizing a stain's titer in a query image to that of a template image.

With reference to FIGS. 2 and 3B, the present disclosure also provides a computer-implemented method of normalizing a stain's titer in an acquired image to a titer level in template image, the method comprising the steps of (a) running an image acquisition module 202 to generate or receive multi-channel image data, e.g. an acquired image, or a biological sample stained with one or more stains; (b) running an unmixing module 205 to generate image channel images corresponding to one or more stain channels; (c) running a FOV generation module 206 to generate FOVs for the test image and, from amongst all the generated FOVs, select those meeting predefined criteria (step 260); running a patch creation module 207 to create a series of patches within each retained FOV and retaining patches meeting certain predefined criteria indicative of the presence of the stain whose titer is to be normalized (step 261); running an transform module 210 to compute transformation coordinates (step 262); running a classification module 211 to determine the probabilities that pixels within a test image belong to a class of pixels denoting the stain whose titer is to be normalized (step 263); and running the transform module 20 to reconstruct an RGB image using weighted transformation coordinates (step 264). In some embodiments, the transform module 210 is a HSD transform module. In some embodiments, the stain is hematoxylin. The skilled artisan will also appreciate that additional modules or databases may be incorporated into the workflow. As will be described in more detail here, in some embodiments, certain parameters for performing an HSD transform may be retrieved from an HSD parameters database 212, as opposed to deriving those parameters during the normalization process. Likewise, an image processing module may be run to apply certain filters to the acquired images or to identify certain histological and/or morphological structures within the tissue samples. In addition, a region of interest selection module may be utilized to select a particular portion of an image for analysis.

Figure 3C:
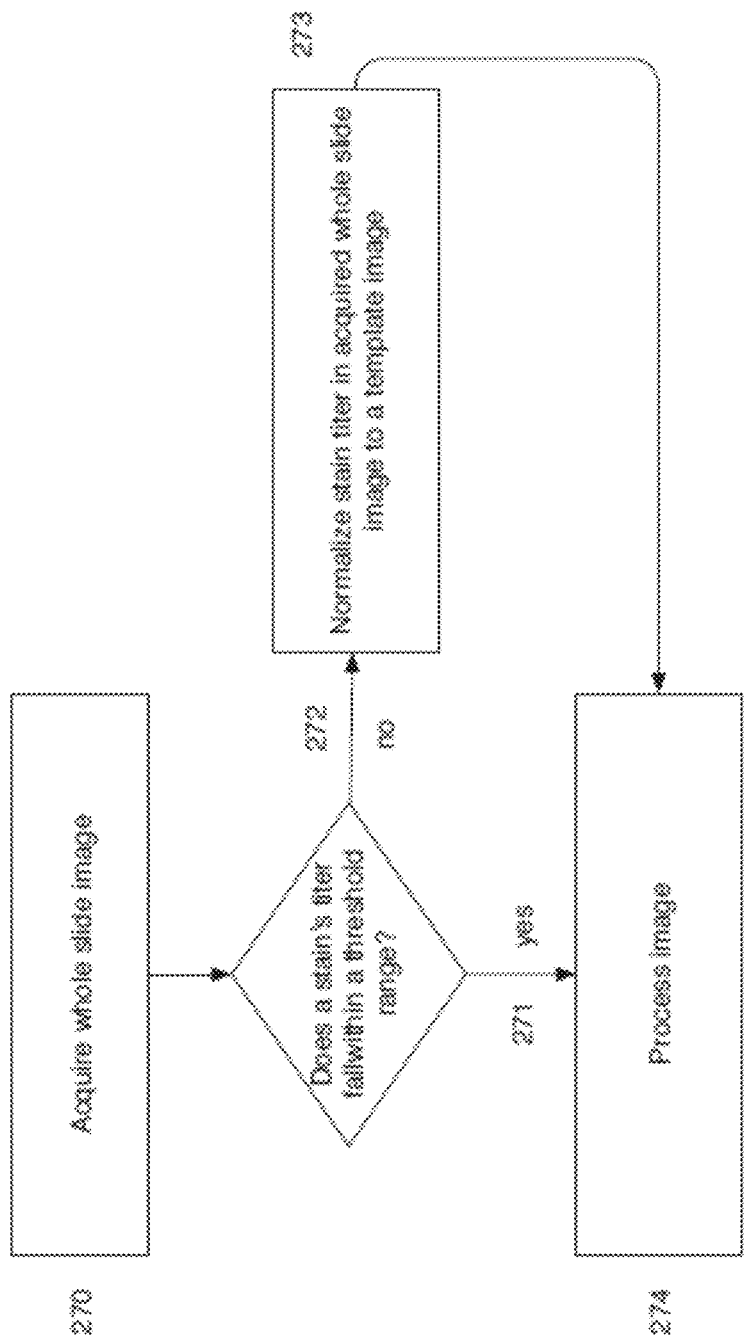
FIG. 3C provides an overview of the steps of assessing a stain titer and then normalizing an image.

In some embodiments, stain titer assessment or estimation is performed prior to normalization. With reference to FIG. 3C, after a whole slide image is acquired (step 270), a stain's titer within the sample is estimated. Then a determination is made as to whether the estimate of the stain's titer falls within a predefined titer threshold, e.g. a threshold ranging from 3 to 6. If the titer does fall within the predefined titer threshold (step 271), the image is ready for further processing (step 273). On the other hand, if the titer does not fall within the predefined titer threshold (step 272), the stain's titer is normalized to that of a template image (step 273).

Figure 3D:
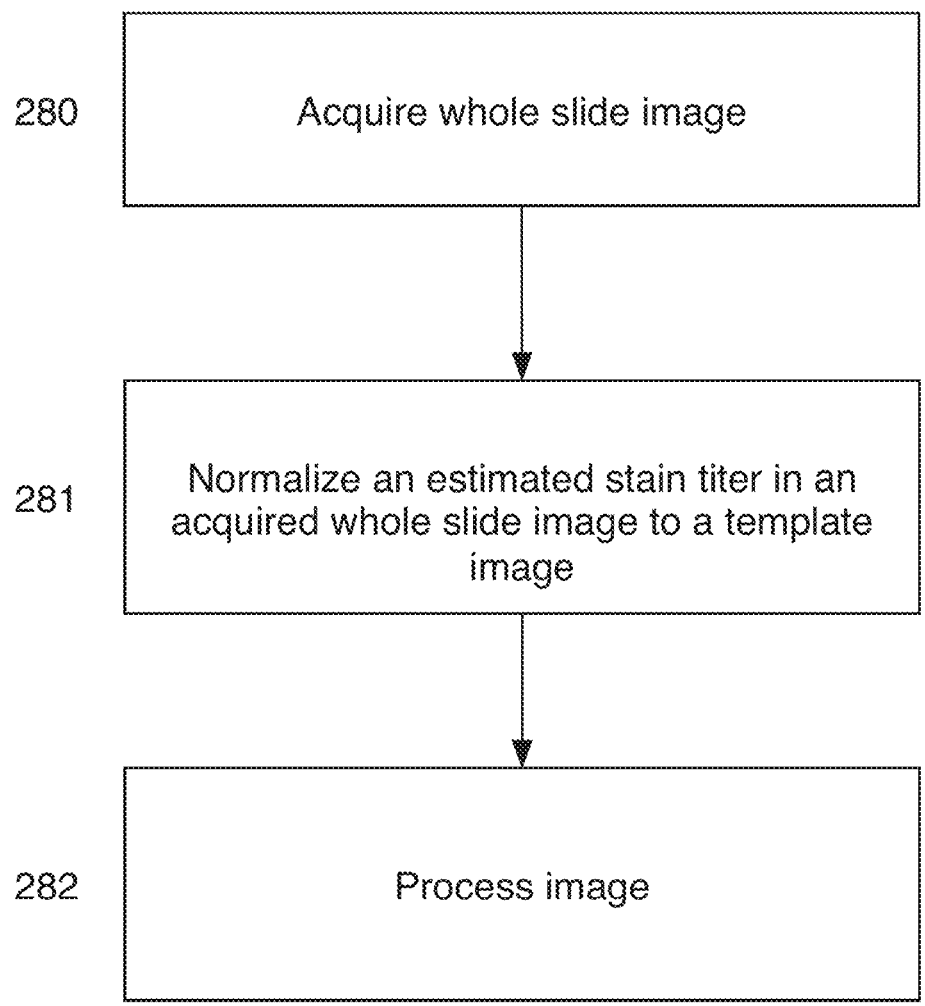
FIG. 3D provides an overview of the steps of assessing a stain titer as part of a normalization process.

In other embodiments, stain titer assessment is run during the normalization process (see, for example, FIG. 3D). For example, in some embodiments, the feature extraction module 208 and the titer classification module 209 may be run to provide an estimate of a stain's titer in a test image during normalization (step 281), such that appropriate parameters tied to a stain's titer may be retrieved from an HSD parameters database 212 for use by the HSD transform module 211. Thus, titer assessment may be run prior to normalization to see if stain titer normalization is needed (see FIG. 3C) or may be run during normalization (FIG. 3D) to retrieve appropriate HSD parameters for performing the alignment and the scaling of the derived chromatic and density distribution coordinates.

The methods described herein may be applied equally to query images and test images. As such, if a particular passage refers to generating FOVs within a query image, those procedures may likewise be applied to template images in the same manner.

Image Acquisition Module

As an initial step, and with reference to FIGS. 2, the digital pathology system 200 runs an image acquisition module 202 to capture images or image data of a biological sample having one or more stains. In some embodiments, the images received or acquired are RGB images or multi-spectral images. In some embodiments, the images captured are stored in memory 201.

The images or image data (used interchangeably herein) may be acquiring using the imaging apparatus 12, such as in real-time. In some embodiments, the images are acquired from a microscope or other instrument capable of capturing image data of a specimen-bearing microscope slide, as noted herein. In some embodiments, the images are acquired using a 2D scanner, such as one capable of scanning image tiles. Alternatively, the images may be images that have been previously acquired (e.g. scanned) and stored in a memory 201 (or, for that matter, retrieved from a server via network 20).

The sample may be stained through application of one or more stains, and the resulting image or image data comprises signals corresponding to each of the one or more stains. As such, while the systems and methods described herein may estimate or normalize to a single stain, e.g. hematoxylin, there exists no limit on the number of stains within the biological sample. Indeed, the biological sample may have been stained in a multiplex assay for two or more stains, in addition to or including any counterstains.

As the skilled artisan will appreciate, a tissue sample may be stained for different types of nuclei and/or cell membrane biomarkers. Methods for staining tissue structures and guidance in the choice of stains appropriate for various purposes are discussed, for example, in "Sambrook et al., Molecular Cloning: A Laboratory Manual, Cold Spring Harbor Laboratory Press (1989)" and "Ausubel et al., Current Protocols in Molecular Biology, Greene Publishing Associates and Wiley-Intersciences (1987)," the disclosures of which are incorporated herein by reference. By way of one non-limiting example, and in the context of detecting breast cancer, in some embodiments the tissue sample is stained in an IHC assay for the presence of one or biomarkers including an estrogen receptor marker, a progesterone receptor marker, a Ki-67 marker, or a HER2 marker. As such, in some embodiments, the biomarker image used as an input is an IHC image which comprises signals corresponding to a presence of at least one of an estrogen receptor (ER) marker, a progesterone receptor (PR) marker, a Ki-67 marker, or a HER2 marker. By way of another non-limiting example, and in the context of detecting non-small cell lung cancer, in some embodiments the tissue sample is stained in an IHC assay for the presence of one or biomarkers including a PD-L1 biomarker. As such, in some embodiments, the biomarker image used as an input is an IHC image which comprises signals corresponding to a presence of a PD-L1 marker, CD3 marker and CD8 marker. In some embodiments, the computer-implemented method further comprises the step of scoring the classified nuclei.

Chromogenic stains may comprise Hematoxylin, Eosin, Fast Red, or 3,3'-Diaminobenzidine (DAB). Of course, the skilled artisan will appreciate that any biological sample may also be stained with one or more fluorophores. In some embodiments, the tissue sample is stained with a primary stain (e.g. hematoxylin). In some embodiments, the tissue sample is stained in an IHC assay for a particular biomarker.

A typical biological sample is processed in an automated staining/assay platform that applies a stain to the sample. There are a variety of commercial products on the market suitable for use as the staining/assay platform, one example being the Discovery™ product of Ventana Medical Systems, Inc. (Tucson, AZ). The camera platform may also include a bright field microscope, one example being the VENTANA iScan HT product of Ventana Medical Systems, Inc., or any microscope having one or more objective lenses and a digital imager, as well as a set of spectral filters. Other techniques for capturing images at different wavelengths may be used. Further camera platforms suitable for imaging stained biological specimens are known in the art and commercially available from companies such as Zeiss, Canon, Applied Spectral Imaging, and others, and such platforms are readily adaptable for use in the system, methods and apparatus of this subject disclosure.

In some embodiments, the input images are masked such that only tissue regions are present in the images. In some embodiments, a tissue region mask is generated to mask non-tissue regions from tissue regions. In some embodiments, a tissue region mask may be created by identifying the tissue regions and excluding the background regions (e.g. regions of a whole slide image corresponding to glass with no sample, such as where there exists only white light from the imaging source). The skilled artisan will appreciate that in addition to masking non-tissue regions from tissue regions, the tissue masking module may also mask other areas of interest as needed, such as a portion of a tissue identified as belonging to a certain tissue type or belonging to a suspected tumor region. In some embodiments, a segmentation technique is used to generate the tissue region masked images by masking tissue regions from non-tissue regions in the input images. Suitable segmentation techniques are as such known from the prior art, (cf. Digital Image Processing, Third Edition, Rafael C. Gonzalez, Richard E. Woods, chapter 10, page 689 and Handbook of Medical Imaging, Processing and Analysis, Isaac N. Bankman Academic Press, 2000, chapter 2). In some embodiments, an image segmentation technique is utilized to distinguish between the digitized tissue data and the slide in the image, the tissue corresponding to the foreground and the slide corresponding to the background. In some embodiments, the component computes the Area of Interest (AoI) in a whole slide image in order to detect all tissue regions in the AoI while limiting the amount of background non-tissue area that is analyzed. A wide range of image segmentation techniques (e.g., HSV color-based image segmentation, Lab image segmentation, mean-shift color image segmentation, region growing, level set methods, fast marching methods, etc.) can be used to determine, for example, boundaries of the tissue data and non-tissue or background data. Based at least in part on the segmentation, the component can also generate a tissue foreground mask that can be used to identify those portions of the digitized slide data that correspond to the tissue data. Alternatively, the component can generate a background mask used to identify those portions of the digitized slide date that do not correspond to the tissue data.

This identification may be enabled by image analysis operations such as edge detection, etc. A tissue region mask may be used to remove the non-tissue background noise in the image, for example the non-tissue regions. In some embodiments, the generation of the tissue region mask comprises one or more of the following operations (but not limited to the following operations): computing the luminance of the low resolution input image, producing a luminance image, applying a standard deviation filter to the luminance image, producing a filtered luminance image, and applying a threshold to filtered luminance image, such that pixels with a luminance above a given threshold are set to one, and pixels below the threshold are set to zero, producing the tissue region mask. Additional information and examples relating to the generation of tissue region masks is disclosed in PCT/EP/2015/062015, entitled "An Image Processing Method and System for Analyzing a Multi-Channel Image Obtained from a Biological Tissue Sample Being Stained by Multiple Stains," the disclosure of which is hereby incorporated by reference herein in its entirety.

Figure 4:
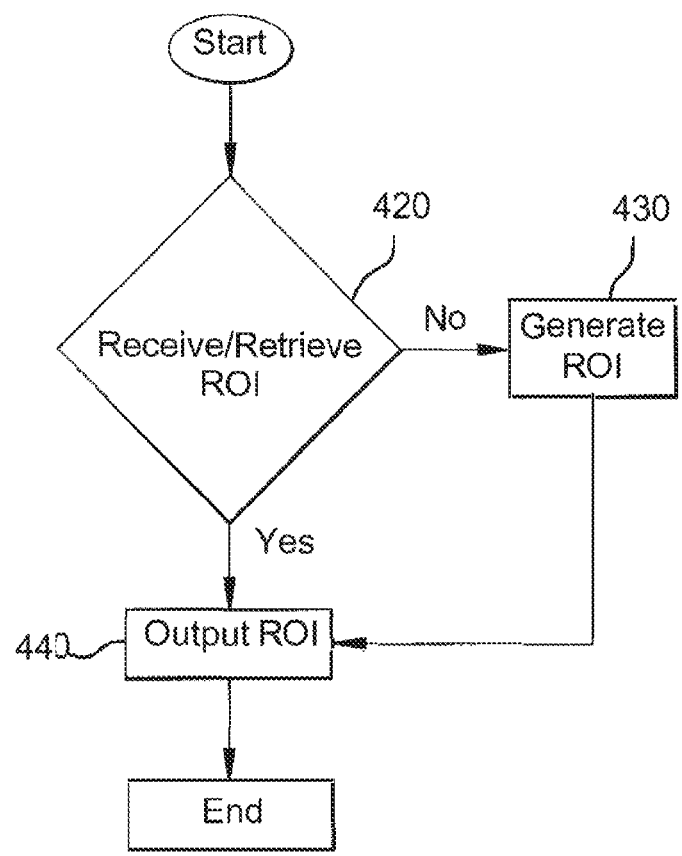
FIG. 4 illustrates an example of FOV selection.

In some embodiments, a region of interest identification module may be used to select a portion of the biological sample for which an image or for which image data should be acquired. FIG. 4 provides a flow chart illustrating the steps of region selection. In step 420, the region selection module receives an identified region of interest or field of view. In some embodiments, the region of interest is identified by a user of a system of the present disclosure, or another system communicatively coupled to a system of the present disclosure. Alternatively, and in other embodiments, the region selection module retrieves a location or identification of a region or interest from a storage/memory. In some embodiments, as shown in step 430, the region selection module automatically generates a FOV or ROI, for example, via methods described in PCT/EP2015/062015, the disclosure of which is hereby incorporated by reference herein in its entirety. In some embodiments, the region of interest is automatically determined by the system based on some predetermined criteria or characteristics that are in or of the image (e.g. for a biological sample stained with more than two stains, identifying an area of the image that comprises just two stains). In step 440, the region selection module outputs the ROI.

Unmixing Module

Following image acquisition, the system 200 receives the multiplexed image as input (e.g. step 280), where the multiplexed image comprises signals corresponding one or more stain channels as described herein. Prior to further processing and analysis, this initial image is first unmixed into its constituent channels, such as with an unmixing module 205, where each unmixed channel corresponds to a particular stain or signal. The unmixed images are hereinafter referred to as "channel images" and may be used as the input for each module described herein.

For example, in a sample comprising one or more stains and hematoxylin, individual images may be produced for each channel of the one or more stains and hematoxylin. Without wishing to be bound by any particular theory, it is believed that these channels highlight different tissue structures in the tissue image, thus, they may be referred to as structural image channels. In some embodiments, unmixing provides at least a hematoxylin image channel image. In some embodiments, an acquired image is unmixed into a separate channel representing the local amounts of hematoxylin and highlighting nuclei regions within the image. The skilled artisan will appreciate that features extracted from these channels are useful in describing the different biological structures present within any image of a tissue.

The multi-spectral image provided by the imaging system 202 is a weighted mixture of the underlying spectral signals associated the individual biomarkers and noise components. At any particular pixel, the mixing weights are proportional to the biomarker expressions of the underlying co-localized biomarkers at the particular location in the tissue and the background noise at that location. Thus, the mixing weights vary from pixel to pixel. The spectral unmixing methods disclosed herein decompose the multi-channel pixel value vector at each and every pixel into a collection of constituent biomarker end members or components and estimate the proportions of the individual constituent stains for each of the biomarkers.

Methods of unmixing are well known to those of ordinary skill in the art and any method now known or later discovered may be used to "unmix" multiplex images into the vessel channel images. In general, the unmixing process extracts stain-specific channels to determine local concentrations of individual stains using reference spectra that are well known for standard types of tissue and stain combinations. The unmixing may use reference spectra retrieved from a control image or estimated from the image under observation. Unmixing the component signals of each input pixel enables retrieval and analysis of stain-specific channels, such as vessel channels and nuclei channels. The terms "unmixing" and "color deconvolution" (or "deconvolution") or the like (e.g. "deconvolving," "unmixed") are used interchangeably in the art.

In some embodiments, the multiplex images are unmixed with unmixing module 205 using liner unmixing. Linear unmixing is described, for example, in 'Zimmermann "Spectral Imaging and Linear Unmixing in Light Microscopy" Adv Biochem Engin/Biotechnol (2005) 95:245-265' and in in C. L. Lawson and R. J. Hanson, "Solving least squares Problems", PrenticeHall, 1974, Chapter 23, p. 161,' the disclosures of which are incorporated herein by reference in their entirety. In linear stain unmixing, the measured spectrum ($S(\lambda)$) at any pixel is considered a linear mixture of stain spectral components and equals the sum of the proportions or weights (A) of each individual stain's color reference ($R(\lambda)$) that is being expressed at the pixel $$S(\lambda) = A_1 \cdot R_1(\lambda) + A_2 \cdot R_2(\lambda) + A_3 \cdot R_3(\lambda) \ldots A_i \cdot R_i(\lambda)$$

which can be more generally expressed as in matrix form as $$S(\lambda) = \Sigma A_i \cdot R_i(\lambda) \text{ or } S = R \cdot A.$$

If there are M channels images acquired and N individual stains, the columns of the M×N matrix R are the optimal color system as derived herein, the N×1 vector A is the unknown of the proportions of individual stains and the M×1 vector S is the measured multichannel spectral vector at a pixel. In these equations, the signal in each pixel (S) is measured during acquisition of the multiplex image and the reference spectra, i.e. the optimal color system, is derived as described herein. The contributions of various stains ($A_i$) can be determined by calculating their contribution to each point in the measured spectrum. In some embodiments, the solution is obtained using an inverse least squares fitting approach that minimizes the square difference between the measured and calculated spectra by solving the following set of equations, $$[\partial \Sigma_j \{S(\lambda_j) - \Sigma_i A_i \cdot R_i(\lambda_j)\}2]/\partial A_i = 0.$$

In this equation, j represents the number of detection channels and i equals the number of stains. The linear equation solution often involves allowing a constrained unmixing to force the weights (A) to sum to unity.

In other embodiments, unmixing is accomplished using the methods described in WO2014/195193, entitled "Image Adaptive Physiologically Plausible Color Separation," filed on May 28, 2014, the disclosure of which is hereby incorporated by reference in its entirety herein. In general, WO2014/195193 describes a method of unmixing by separating component signals of the input image using iteratively optimized reference vectors. In some embodiments, image data from an assay is correlated with expected or ideal results specific to the characteristics of the assay to determine a quality metric. In the case of low quality images or poor correlations against ideal results, one or more reference column vectors in matrix R are adjusted, and the unmixing is repeated iteratively using adjusted reference vectors, until the correlation shows a good quality image that matches physiological and anatomical requirements. The anatomical, physiological, and assay information may be used to define rules that are applied to the measured image data to determine the quality metric. This information includes how the tissue was stained, what structures within the tissue were intended or not intended to be stained, and relationships between structures, stains, and markers specific to the assay being processed. An iterative process results in stain-specific vectors that can generate images that accurately identify structures of interest and biologically relevant information, are free from any noisy or unwanted spectra, and therefore fit for analysis. The reference vectors are adjusted to within a search space. The search space defines a range of values that a reference vector can take to represent a stain. The search space may be determined by scanning a variety of representative training assays, including known or commonly occurring problems, and determining high-quality sets of reference vectors for the training assays.

In other embodiments, unmixing is accomplished using the methods described in WO2015/124772, entitled "Group Sparsity Model for Image Unmixing," filed on Feb. 23, 2015, the disclosure of which is hereby incorporated by reference in its entirety herein. In general, WO2015/124772 describes unmixing using a group sparsity framework, in which fractions of stain contributions from a plurality of colocation markers are modeled within a "same group" and fractions of stain contributions from a plurality of non-colocation markers are modeled in different groups, providing co-localization information of the plurality of colocation markers to the modeled group sparsity framework, solving the modeled framework using a group lasso to yield a least squares solution within each group, wherein the least squares solution corresponds to the unmixing of the colocation markers, and yielding a sparse solution among the groups that corresponds to the unmixing of the non-colocation markers. Moreover, WO2015/124772 describes a method of unmixing by inputting image data obtained from the biological tissue sample, reading reference data from an electronic memory, the reference data being descriptive of the stain color of each one of the multiple stains, reading colocation data from electronic memory, the colocation data being descriptive of groups of the stains, each group comprising stains that can be collocated in the biological tissue sample, and each group forming a group for the group lasso criterion, at least one of the groups having a size of two or above, and calculating a solution of the group lasso criterion for obtaining the unmixed image using the reference data as a reference matrix. In some embodiments, the method for unmixing an image may comprise generating a group sparsity model wherein a fraction of a stain contribution from colocalized markers is assigned within a single group and a fraction of a stain contribution from non-colocalized markers is assigned within separate groups, and solving the group sparsity model using an unmixing algorithm to yield a least squares solution within each group.

FOV Extraction Module

In some embodiments, the entire whole slide image, or a region thereof, is subdivided into a plurality of FOVs to generate an FOV sampling grid (steps 250 or 260). The FOV sampling grid is generated in order to have a set of representative regions within the image that can be compared against one another. In some embodiments, the FOVs are distributed across the image in a manner that captures a representative sample of relevant regions for analysis. One way that this can be accomplished is to automatically or manually generate a regularly spaced grid of FOVs to provide an unbiased structured sampling over the image. In some embodiments, the grid covers the entire image. In other embodiments, the grid covers less than the entire image.

Typically, a FOV size is chosen such that a FOV can be presented on a computer screen at full resolution. For example, if a computer screen offers 1000×1000 pixels resolution and the pixel in the whole-slide image is 0.5 micrometer×0.5 micrometer, then a good FOV candidate size is also 1000×1000 pixels or 0.5 mm×0.5 mm in size.

In some embodiments, a predefined number of FOV are extracted from the whole slide image. In some embodiments, the predefined number of FOV range from 25 to 100. In other embodiments, the predefined number of FOV is about 50. In some embodiments, the predefined number of FOV are selected based on a feature of a stain within the image. In some embodiments, the predetermined FOVs are selected based on a predetermined stain intensity level, e.g. a hematoxylin intensity level.

In some embodiments, the channel according to the stain whose titer is to be assessed is then used to derive an image histogram (e.g. if the stain whose titer is to be assessed is hematoxylin, then an image histogram corresponding to the hematoxylin channel will be generated). In some embodiments, for each FOV within the generated grid, the mean pixel intensity is calculated (using the derived histogram) and those FOV that meet a certain predetermined mean stain intensity are retained. In other embodiments, the mean pixel intensity is calculated for each FOV and those FOV that are within a top predefined percentage of a mean pixel intensity are retained. In some embodiments, the stain is hematoxylin and FOV are selected that meet an 80% intensity level for hematoxylin. In some embodiments, this is done based on the assumption that relatively strong hematoxylin stain represents the stain in a cell nucleus. In some embodiments, an 80% percentile is empirically chosen to reduce the risk of bias caused by extremely high hematoxylin outliers.

Patch Creation and Retention Module

Once the FOV are extracted from the image, a series of patches are generated within each FOV (steps 251 and 261). Just as with FOV creation, the patches may be produced by generating a sampling grid, i.e. automatically or manually generating a regularly spaced grid of patches to provide an unbiased structured sampling within the FOV. In some embodiments, the patches have (x, y) dimensions which range from about 5% to about 20% of the size of the dimensions of the FOV. For example, if a FOV has a size of 1000 pixels×1000 pixels, then each patch within the FOV may have a size of 100 pixels×100 pixels. The skilled artisan will appreciate that multiple, non-overlapping patches will be derived for each FOV.

In some embodiments, the patches generated are in the form of "superpixels." Superpixels are sub-areas of an image covering multiple adjacent pixels. "Superpixels" divide the image into non-intersecting image patches with a freeform shape. In some embodiments, the shape may be chosen such that each superpixel meets a target size range and contains predominantly tissue or cells of one type. Superpixels may be generated by many methods including "graph-based algorithms," "gradient-ascent-based algorithms," a SLIC algorithm, mean shift, and normalized cuts. Thus, according to embodiments, a superpixel-generation procedure may be applied on the image for generating the patches, each patch being a superpixel. According to embodiments, simple linear iterative clustering is used in order to identify adjacent pixel sets to be used as the "patches" (i.e., superpixels). Simple linear iterative clustering (SLIC) is an adaptation of k-means for superpixel generation, with two important distinctions:

(i) the number of distance calculations in the optimization is dramatically reduced by limiting the search space to a region proportional to the superpixel size (this is believed to reduce the complexity to be linear in the number of pixels—and independent of the number of superpixels k); and (ii) a weighted distance measure combines color and spatial proximity while simultaneously providing control over the size and compactness of the superpixels. (See Achanta, et al., "SLIC Superpixels Compared to State-of-the-Art Superpixel Methods," IEEE Transactions on Pattern Analysis and Machine Intelligence, Vol. 34, No. 11, November 2012, the disclosure of which is hereby incorporated by reference in its entirety herein). For example, the region proportional to the superpixel size may be identical to a predefined upper limit of the super pixel area used for identifying the superpixels.

In some embodiments, only those patches within an FOV that meet certain predefined criteria are retained for further analysis. For example, patches that do not have any cells in them (background patches) should not have any stain and consequently it is believed that they would not have any useful information for titer level determination.

In some embodiments, a first requirement is that a certain predefined percentage of all pixels within the patch must have a signal corresponding to that stain whose titer is being assessed, and this is determined using that stain's image channel (e.g. if the stain is hematoxylin, then the hematoxylin channel is utilized). In some embodiments, the predefined percentage of stain pixels is at least 60%. In other embodiments, the predefined percentage of stain pixels is at least 65%. In yet other embodiments, the predefined percentage of stain pixels is at least 70%. In further embodiments, the predefined percentage of stain pixels is at least 75%. For example, if a patch size is 100 pixels×100 pixels, and the threshold percentage is set at 70%, then of the 10,000 pixels within the patch 7,000 must be representative of the stain to be assessed, for hematoxylin.

In some embodiments, another requirement is that a certain predefined percentage of all pixels must have some staining. A pixel is considered "white" if the three color channels in RGB color space each have a value greater than 200 (assuming each channel has 8-bits). The skilled artisan will appreciate that if the RGB image is 24-bit, each channel has 8 bits, for red, green, and blue—in other words, the image is composed of three images (one for each channel), where each image can store discrete pixels with conventional brightness intensities between 0 and 255. In some embodiments, the predefined percentage of pixels that must have staining is at least 40%, i.e. at least 40% of the pixels must have RGB channel values of less than 200 each. In other embodiments, the predefined percentage of pixels that must have staining is at least 45%. In yet other embodiments, the predefined percentage of pixels that must have staining is at least 50%. In further embodiments, the predefined percentage of pixels that must have staining is at least 60%.

Yet another requirement is that a certain predefined percentage of all pixels must be arranged in a "cell-like" structure. In some embodiments, the predefined percentage of all pixels that must be arranged in a cell-like structure is at least 25% of all pixels in the acquired image or in any selected portion thereof. In other embodiments, the predefined percentage is at least 30%. In yet other embodiments, the predefined percentage ranges from between about 30% and about 35%.

In some embodiments, difference of Gaussian (DoG) filtering is used to identify such cell-like structures. In general, difference of Gaussians is a feature enhancement algorithm that involves the subtraction of one blurred version of an original image from another, less blurred version of the original. In the simple case of grayscale images, the blurred images are obtained by convolving the original grayscale images with Gaussian kernels having differing standard deviations. It is believed that blurring an image using a Gaussian kernel suppresses only high-frequency spatial information. Subtracting one image from the other preserves spatial information that lies between the range of frequencies that are preserved in the two blurred images. Thus, the difference of Gaussians is a band-pass filter that discards all but a handful of spatial frequencies that are present in the original grayscale image.

In some embodiments, a multi-scale DoG is implemented by considering Gaussian kernels with progressively decreasing standard variation, and by considering the difference between the images obtained after filtering with two consecutive Gaussians, whereby "blob-like" structures having a certain radii range are expected to be detected. In some embodiments, the 0th-layer in the multi-scale DoG corresponds to the image obtained after taking the difference between the image filtered with the coarsest Gaussian (Gaussian with maximum standard deviation) and the image filtered with the next coarsest Gaussian (Gaussian with the next highest standard deviation) (referred to herein as a "difference of Gaussian image" or "DoG image"). For example, a 0th-layer DoG image may be computed as a difference-of-Gaussian of a first Gaussian filter pair, the first Gaussian filter pair comprising a first filter with a standard deviation of 1 and a second Gaussian filter with a standard deviation of 2. A 1st-layer DoG image may be computed as a difference-of-Gaussian of a second Gaussian filter pair, the second Gaussian filter pair comprising a first filter with a standard deviation of 2 and a second Gaussian filter with a standard deviation of 3. A 2nd-layer DoG image may be computed as a difference-of-Gaussian of a third Gaussian filter pair, the third Gaussian filter pair comprising a first filter with a standard deviation of 3 and a second Gaussian filter with a standard deviation of 4. The standard deviations need not be integer values and other standard deviation values in a similar range may be used in other embodiments of the disclosure. The radius and shape of the Kernels of the Gaussian filters may be chosen such that a filter pair will generate DoG of high magnitude for blobs of an expected size and shape.

In other embodiments, a generalized Laplacian of Gaussian filter may be utilized to detect blobs within the image, and hence to detect cell-like structures. Such an approach is described by Kong, "A Generalized Laplacian of Gaussian Filter for Blob Detection and Its Applications," IEEE Trans Cybern. 2013 December; 43(6): 1719-33, the disclosure of which is hereby incorporated by reference herein in its entirety.

Feature Extraction Module

Following the retention of those patches that contain data indicative of a stain (step 251) using the patch creation and retention module 207, color and intensity features indicative of the stain whose titer is being assessed are derived (step 252).

In some embodiments, features derived from color include color ratios, $R/(R+G+B)$. or color principal components. In other embodiments, metrics derived from color include local statistics of each of the colors (mean/median/variance/std dev) and/or color intensity correlations in a local image window. In some embodiments, the features include mean, median, first quartile, third quartile, first invariant moment, and standard deviation values derived from (a) a first stain channel image after color deconvolution, (b) a low pass version of the whole slide image; (c) an absorbance image; and (d) the L and B image channels from LAB decomposition. In some embodiments, the features are derived from image histograms of each of the aforementioned derived images or image channel images. The skilled artisan will appreciate that the histogram of an image normally refers to a histogram of the pixel intensity values. This histogram is a graph showing the number of pixels in an image at each different intensity value found in that image. For an 8-bit grayscale image there are 256 different possible intensities, and so the histogram will graphically display 256 numbers showing the distribution of pixels amongst those grayscale values. Histograms can also be taken of color images—for example, individual histograms of red, green and blue channels can be taken.

In some embodiments, a generated image histogram derived from an unmixed image channel image may be used to calculate features including, but not limited to, the mean, median, first quartile, and third quartile values. In some embodiments, a standard deviation is also calculated as a feature based on the histogram of intensity values derived from the stain channel image.

In some embodiments, an absorbance image is computed from within the optical density domain representation of an RGB image of the acquired image. In some embodiments, a histogram of the absorbance image is generated and utilized for deriving mean, media, first quartile, third quartile, and standard deviation values.

The LAB color space contains one luminance channel, L, and 2 chrominance channels, A and B. In the L*a*b color space, the "L" channel represents the brightness of a pixel, the "A" channel reflects the red and green components of a pixel, and the "B" channel represents the blue and yellow components of a pixel. In some embodiments, histograms for the L channel and for the B channel are used to calculate the mean, median, first quartile, and third quartile values. In some embodiments, the first invariant moment is calculated from the histogram of intensity values derived from the L and B channels after LAB decomposition.

In some embodiments, a low pass filter may be applied to the stain channel image. A low pass filter, for example, is a filter that smooths the first stain channel image, thereby replacing each pixel value with a pixel value that averages or otherwise represents the pixel values in a local neighborhood around each pixel. In some embodiments, a histogram for the low pass filtered first stain channel image is used to calculate the mean, median, first quartile, and third quartile values.

In some embodiments, features include the first and third quartiles derived from an image histogram. The first and third quartiles are descriptive statistics that are measurements of position in a data set. In some embodiments, the first and third quartiles are derived by sorting the pixel intensity data in the histogram, such as in ascending order. The first quartile, or lower quartile, is the value that cuts off the first 25% of the pixel intensity data when it is sorted in ascending order. The pixel intensity data value that is in the center of this list (or the average of the two values in the center of the list) represents the first quarter. Likewise, the third quartile, or upper quartile, is the value that cuts off the first 75%. The pixel intensity data value that is in the center of this list (or the average of the two values in the center of the list) represents the third quarter.

In some embodiments, the features include first invariant moments. An image moment is a certain particular weighted average (moment) of the image pixels' intensities, or a function of such moments, usually chosen to have some attractive property or interpretation. Color moments are measures that characterize color distribution in an image. The first color moment can be interpreted as the average color in the image, and it can be calculated by using the following formula:

$$E_i = \Sigma_{j=1}^{N} \frac{1}{N} p_{ij}$$

where N is the number of pixels in the image and $p_{ij}$ is the value of the j-th pixel of the image at the i-th color channel.

In some embodiments, the feature is a standard deviation value of an image histogram is calculated by first deriving the mean pixel intensity value from the histogram, and then taking the square root of the mean pixel intensity value.

Titer Classification Module

Following derivation of the stain color and intensity features (step 252) using the feature extraction module 208, derived features are then provided to a classifier module such that a titer level of the stain within each derived image patch may be computed (steps 253 and 254).

Machine learning algorithms (a classifier) may comprise ensemble learning methods that incorporate a plurality of the machine learning methods described herein to obtain better predictive performance than can be achieved from any one of the machine learning methods described herein. The ensemble learning methods can comprise, without limitation, Bayes optimal classifiers, bootstrap aggregating ("bagging"), boosting, Bayesian model averaging, Bayesian model combination, cross-validation selection ("bucket of models"), stacking (stacked generalization), and random forests. In some embodiments, the ensemble learning method comprises random forests that operate by constructing a plurality of decision trees and outputting the class that is the mode of the classes (classification) or mean prediction (regression) of the individual trees.

A "classifier" as used herein is a program logic capable of identifying to which of a set of categories (object classes) a new observation (an object) belongs by analyzing property values, also referred to as "object feature values" or "explanatory variables," of the new observation to be categorized. A classifier may be obtained on the basis of a training set of data containing observations on whose category membership is known (here, training images derived from slides having known stain titer levels). In some embodiments, the classifier is obtained by means of applying a supervised learning approach, e.g. by training an untrained version of a classifier on a training set of correctly identified stain titer levels, whereby the number and type of object classes is known in advance.

In some embodiments, the classifier is a random forest classifier. For example, the random forest classifier may be trained by: (i) creating a training set of digital images having known, different titer levels; (ii) extracting image features indicative of the first stain from the training set of digital images (e.g. color and intensity features of a stain), such as described herein using at least modules 205 through 208; and (iii) training the random forest classifier to identify a titer level based on the set of extracted features (such as those features noted above relating to stain color features and stain intensity features), using titer levels as class labels. The trained random forest classifier may then be applied to classify derived stain color and intensity features (step 253) within derived image patches of a test image to determine an estimate titer value for the particular patch. In some embodiments, training images are utilized. The training slide/image can be generated from any tissue samples. In some embodiments, the training is tissue specific and only hematoxylin stain is applied.

In some embodiments, a plurality of training images having different titer levels is provided to a classifier for training. Each training digital image may be an RGB image having a predetermined titer score known to accurately indicate the tier of the first stain. For each of the training digital images, the system computes a plurality of image features indicative of the first stain (such as described herein). Here, stain color and stain intensity features and associated slide titer levels are used to train a random forest classifier.

After the classifier 209 is trained, it is used to classify patches within test images having unknown titer levels (step 253). The output of the classifier is a numerical score for each patch, i.e. an estimated titer score for each patch, the estimated titer score ranging from 1 to 9, with 1 representing the lowest level (lightest staining) and 9 representing the highest level (darkest staining) (these may be integers or any fraction thereof).

In some embodiments, a score for the whole slide image is then obtained from the individual titer scores of each patch (step 254). In some embodiments, the score for the whole slide image is a weighted average of the titer scores from the classified patches. For example, if 50 patches were considered and 20 of those patches had a titer score of 1 and 30 of those patches had a titer score of 9, then then ((20*1)+(30*9))/50=5.8, where the score of 5.8 would represent the weighted average score for the whole slide image (test image). In some embodiments, an alternative method of computing the score is to take the mode of the patch score histogram. For example, if among the 50 patches, there are 10 patches have score 1, 10 patches have score 3, and 30 patches have score 4, then the mode score of the whole slide is 4.

With reference to FIG. 3C, in some embodiments, this weighted average score (or mode score) may be compared to a predetermined titer threshold. If the weighted average (mode) score is within the limit defined by the predetermined titer threshold, then normalization is not needed (step 271). On the other hand, if the weighted average score does not fall within the limit defined by the predetermined titer threshold (step 272), then normalization may be needed, such as described further herein. In some embodiments, the predetermined titer threshold ranges from between about 3.5 to about 6.5.

HSD Transformation Module

According to some aspects of the present disclosure, an HSD transformation module 210 may be utilized to normalize a titer of a stain in an input image (a "query" image) to a titer of a stain in a template image. The resulting normalized image may then be used for further processing, e.g. nuclear and/or morphological features may be identified, classified, and scored using a normalized image.

With reference to FIG. 3B, the HSD transformation module 210 is responsible for (i) deriving initial chromatic and density distribution coordinates for each pixel within each retained patch in a query image (within a HSD color model) (step 262); (ii) matching the derived chromatic and density distribution coordinates from the query image with template chromatic and density distribution coordinates to determine transformation coordinates for each pixel within each retained patch in the query image (step 263), and (iii) upon receiving stain probability values from the HSD classification module 211, regenerate an RGB from the query image in the HSD color model using final transformation coordinates for each pixel within each patch, the final transformation coordinates weighted by the received probability values (step 264). Each of these steps will be described in further detail herein.

As noted herein, there are situations where titer normalization is performed without first assaying stain titer, i.e. the titer assaying steps are not performed before normalization, but may be performed during normalization such that an estimated titer of a stain in a slide may be ascertained in order for suitable alignment and scaling parameters may be derived or retrieved, as described further herein. In these situations, prior to running the HSD transformation module 210, the FOV generation module 206 and patch creation and retention module 207 are run. As noted herein, it is within the retained patches that the HSD coordinates for image pixels are computed. Each of the procedures from steps 250 and 251 as outlined herein, may be repeated for normalization steps 260 and 261. Without repeating the procedures outlined herein, an acquired image may be divided into a grid of FOV. Of the entire grid of FOV, FOV are retained meeting a threshold criteria, e.g. an 80% stain intensity level. Within each of the retained FOV, patches are created and patches are retained meeting certain predefined criteria of a stain, as denoted herein.

Derivation of HSD Coordinates ($c_x$, $c_y$, D)

The Hue-Saturation-Density (HSD) color model is derived from the Hue-Saturation-Intensity color model. The idea behind the HSD color model is to apply a RGB to HSI transform (hue-saturation-intensity transform) to optical densities (OD) for the individual RGB channels instead of intensities. As the skilled artisan will appreciate, direct use of the three intensities obtained by a color camera results in the RGB color model. As the chromatic component of the HSD model is independent of the amount of stain, the obtained colorimetric space is believed to better discriminate between the absorption characteristics of the different stains. By decoupling the intensity from the RGB data, the HSI color model is obtained. Without wishing to be bound by any particular theory, it is believed that the major part of the variation in perceived intensities in transmitted light microscopy is caused by variations in staining density. Therefore, the HSD transform is defined as the RGB to HSI transform, applied to optical density values rather than intensities for the individual RGB channels.

The HSD model transforms RGB data into two chromatic components ($c_x$, $c_y$) which are independent of the amount of stain; and a density component (D; which is linearly related to the amount of stain). Without wishing to be bound by any particular theory, it is believed that theoretical RGB intensities obtained from varying stain densities should result in a single point in the chromaticity ($c_x$, cy) plane of the HSD transform. As a result, it is believed that the chromatic data of the pixels stained with a particular stain (e.g. hematoxylin) will form a distribution, which is represented by F($c_x$, $c_y$).

Figure 6:
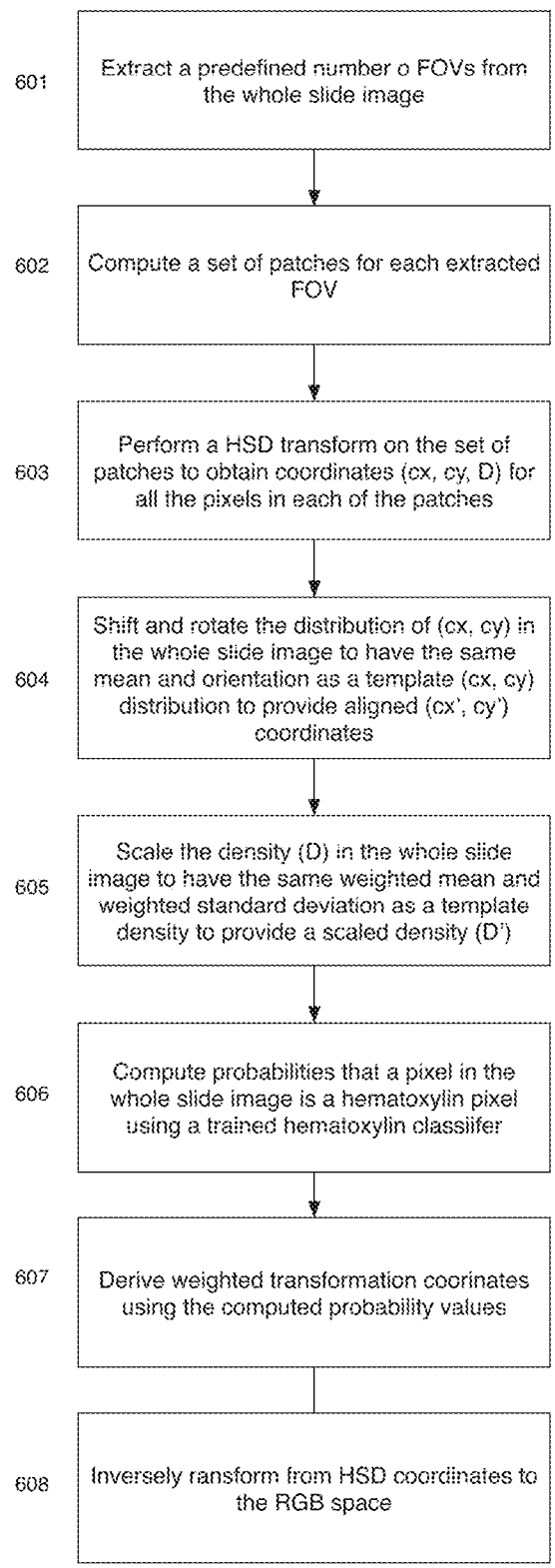
FIG. 6 illustrates the steps for normalizing a titer of a stain in a query image to a titer of the same stain in a template image.
Figure 7:
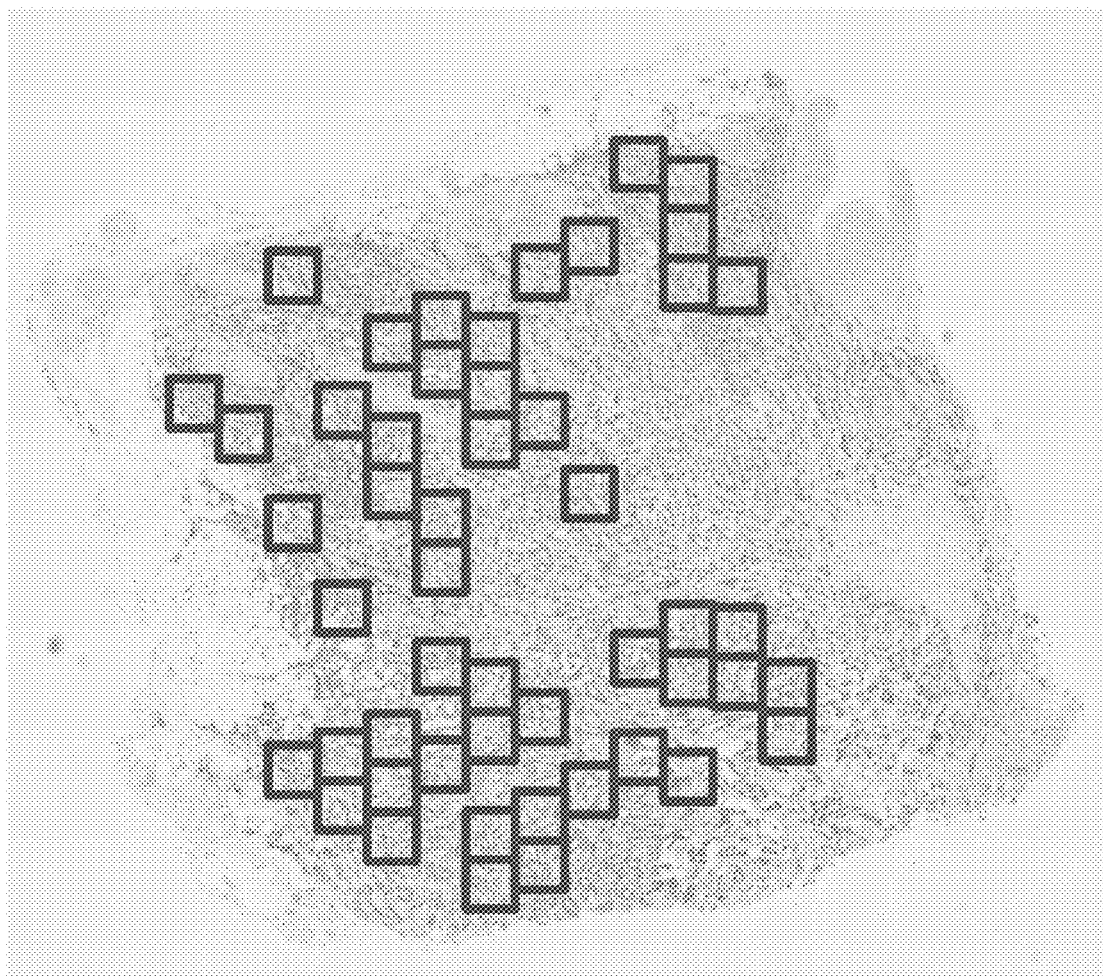
FIG. 7 provides an example whole slide (low magnification) image and after 50 FOVS are superimposed over the whole slide image. The 50 FOVS (red squares) are selected as the closest to the 80% hematoxylin level of the whole slide.

With reference to FIG. 6, following FOV and patch creation (steps 601 and 602), the HSD coordinates of each pixel within each retained patch are calculated (step 603), thus providing the chromatic and density distribution coordinates ($c_x$, $c_y$, D) for each pixel. This is achieved by performing an HSD transform of an input RGB image. As an initial matter, the skilled artisan will appreciate that the detected intensities of light transmitted through a specimen and the amount (A) of stain with absorption factor c is described by Lambert-Beer's law $I=I_0 \cdot e^{-A \cdot c}$. The optical density (OD) for red, green and blue spectral bands is then defined by equation (1):

$$OD_{ch} = A \cdot c_{ch} = -\ln\left(\frac{I_{ch}}{I_{0ch}}\right), \text{ where } ch \in \{R, G, B\} \quad (1)$$

The optical density for a channel $_{Dch}$ depends linearly on the amount of stain, given the absorption value of the stain at channel ch. In some embodiments, the overall intensity of the RGB signal is defined as in equation (2)

$$I = \frac{I_R + I_G + I_B}{3}. \quad (2)$$

Analogously, an overall measure for the OD can be defined as in equation (3)

$$D = \frac{D_R + D_G + D_B}{3} = \frac{A \cdot (c_R + c_G + c_B)}{3}. \quad (3)$$

Figure 5A:
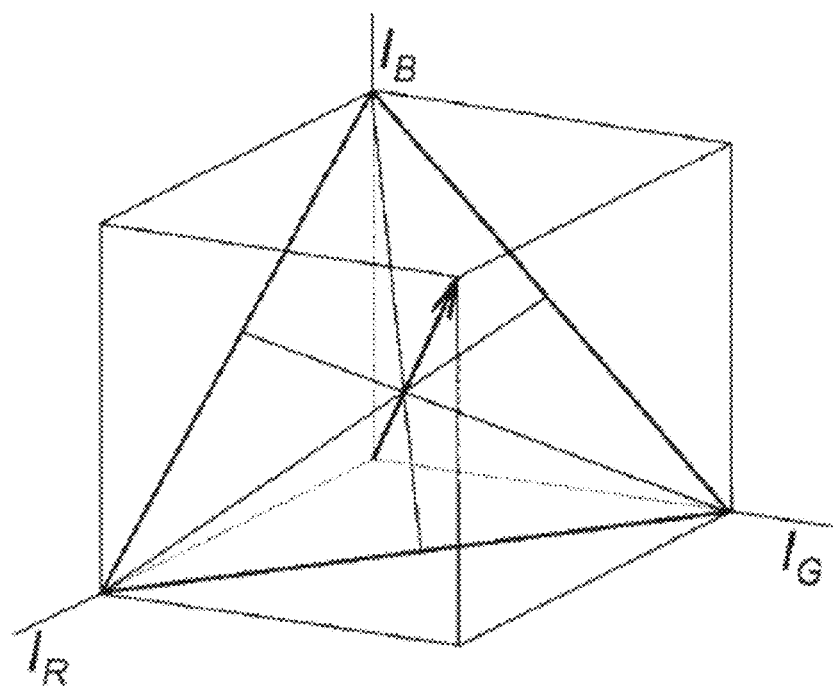
FIG. 5A illustrates that a RGB camera signal can be viewed as a 3D coordinate space. Camera limitations limit the space to a cube (a RGB cube); also shown is the triangle with constant overall intensity equal to the maximum of the individual channel intensities.

With reference to FIG. 5A, the origin of the RGB space represents black (i.e., all three primary intensities are zero), and the farthest corner of the cube represents white (all primary intensities maximal). The line connecting those extremes represents all grey values. Each composite color is represented by a point in this cube. The intensity of a composite color is defined as $I=(I_R+I_G+I_B)/3$ the average of the three primary intensities. In the RGB cube, each plane perpendicular to the grey-scale diagonal has the property that points located on the plane have equal intensity (FIG. 5A shows one such plane). Points on such a plane are limited to a triangular domain, of which the size linearly depends on the value of I for the particular plane. The grey-scale diagonal intersects this triangle in the center of gravity. It is possible to normalize this equilateral chromaticity triangle to a standardized size, making the coordinates of a point on this plane independent of the intensity.

Again, with reference to FIG. 5A, in the chromaticity triangle, a 2D coordinate system ($c_x$, $c_y$) can be defined with the center of gravity as origin and with the positive x-axes through the corner where the red intensity is maximal. Every point in the RGB space can be transformed to its chromaticity coordinates, which are independent of the intensity. For every two RGB points having the same chromaticity coordinates, the ratios between the RGB intensities are identical. Calculation of the chromatic coordinates requires projection of the RGB data onto the triangle (see FIGS. 5A and 5B).

Figure 5B:
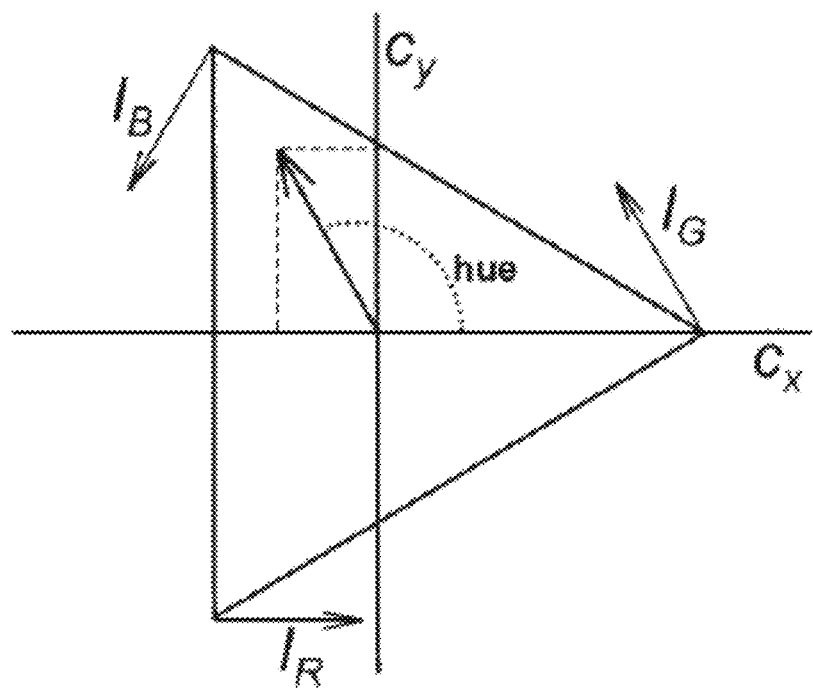
FIG. 5B illustrates the plane resulting from a project of RGB data.

By using the projection from FIGS. 5A and 5B on the optical densities of the three channels (see Eq. 3) the RGB to HSD transform is defined as follows:

$$c_x = \frac{D_R}{D} - 1$$

$$c_y = \frac{D_G - D_B}{\sqrt{3} \cdot D}$$

For the HSD model, the resulting ($c_x$, $c_y$) plane has the property that single points result from RGB points with identical ratios between the $c_R$, $c_G$, and $c_B$. Thus, all information regarding the absorption curves is represented in a single plane.

The optical density for a channel can be defined as:

$$D_{ch} = -\ln\left(\frac{I_{ch}}{I_{0,ch}}\right),$$

where $I_{0,ch}$ is the intensity of a channel ch when no stain is present.

An overall measure for the optical density can be defined as:

$$D = \frac{D_R + D_R + D_B}{3}$$

Derivation of Transformation Coordinates ($c_x'$, $c_y'$, D')

Following the derivation of the HSD coordinates, i.e. performing an RGB image to HSD transform, for each pixel within each retained patch (step 603), the transformation coordinates ($c_x'$, $c_y'$, D') are derived. In general, the chromatic distribution coordinates ($c_x$, $c_y$) for each pixel in each patch of the test image are matched (aligned) with chromatic distribution coordinates in a template image to provide chromatic distribution transformation coordinates ($c_x'$, $c_y'$) (step 604). Likewise, the density distribution coordinates (D for each pixel in each patch for the test image are matched with (scaled to) density distribution coordinates in a template image to provide density distribution transformation coordinates (D') (step 605). The steps of alignment (including derivation of parameters for performing the alignment) and scaling are described herein.

Transformation of the Derived Coordinates

To transform the chromatic and density distribution coordinates of the test image to match the corresponding class distribution in the template image (step 604), a 2D registration of the color information in the (cx, cy) plane is performed. F(cx, cy) is used to denote the chromatic distribution such that the registration problem may be defined as fined the transformation function T such that:

$$F(T(c_x, c_y)) \sim F_{template}(c_x, c_y).$$

The procedure for registration of the chromatic distribution has two steps: (1) extraction of statistical parameters from the template slide, and (2) transforming the 2D chromatic distribution as described below.

Statistical Parameter Derivation/HSD Parameter Database

Statistical parameters are needed to derive transformation coordinates for both the alignment and scaling steps described herein. The statistical parameters may be derived or retried from a HSD parameter database 212.

In some embodiments, the statistical parameters derived include the mean (µ) and angle (ø) of stain class distributions in a template image. In some embodiments, the angle (ø) of a stain-class distribution, e.g. hematoxylin, with respect to the $c_x$ axis is derived by calculating a major eigenvector. In some embodiments, a first eigenvector of the covariance matrix of the ($c_x$, $c_y$) pairs is solved; and the angle is solved in the 2D chromatic space. In some embodiments, the statistical parameters also include scaling parameters. In some embodiments, the scaling parameters are derived by translating the entire $F_{template}$ distribution to the origin (see, FIGS. 5A and 5B), followed by a rotation step along the angle (ø) to maximize the variance along the $c_x$ axis. Finally, the scaling parameters are defined after projection of the rotated distribution onto each of the $c_x$ and $c_y$ axes, comprising the minimum, $1^{st}$, $25^{th}$, $50^{th}$, $75^{th}$, and $99^{th}$ percentiles, and maximum of the projected values along each axis. Methods of deriving each of the statistical parameters is further disclosed within J. A. van der Laak, "Hue-saturation-density (HSD) model for stain recognition in digital images from transmitted light microscopy," cytometry, vol. 39, no. 4, pp. 275-284, 2000, the disclosure of which is hereby incorporated by reference herein in its entirety.

The skilled artisan will appreciate that the derivation of the statistical parameters for the alignment of the chromatic distribution coordinates and for the scaling of the density distribution coordinates can be quite computationally taxing. The skilled artisan will also appreciate if data is generated from a controlled source, then it is possible to reduce variance in the analysis. Indeed, is possible to reduce variance from tissue sources, leaving the only stain variance. Therefore, in an effort to expedite computation time, reduce compotation costs, and reduce biases associated with tissue type, pathology, etc., Applicants propose the use of a database of standardized "look-up" values for these statistical parameters, the statistical parameters derived from tissues stained according to assay standards. Without wishing to be bound by any particular theory, it is believed that if we have bias or error in the estimation of the parameters, the normalization may be "off" and the resulting normalized image may become worse in terms of image quality. For example, if an image is very dark due to biological causes and not due to the staining procedure and we capture this in the normalization parameters then, upon normalization, the image will lose its biological meaning.

In some embodiments, a database of statistical parameters includes look-up values for each of a series of different titers for the stain being normalized. Indeed, the data base may include statistical parameters for a stain at titer levels 1 through 9. For example, the database may comprise mean, angle, scaling parameters, etc. for a first stain at a titer of 4. The database may also comprise mean, angle, scaling parameters, etc. for the first stain at a titer of 5. Likewise, mean, angle, scaling parameters, etc. for $2^{nd}$, $3^{rd}$, . . . nth stains at titer levels ranging from 1 to 9. The skilled artisan will also appreciate that statistical parameters may also be provided for fractions of any titer level, e.g. a titer estimated to be about 4.5. In some embodiments, the parameters are extracted from a set of slides using FOVs and patches as explained above. Then these images are classified with the titer-classification algorithm, and the resulting predicted titer is associated to the extracted parameter. When a new slide comes in, it will be classified and the result will be used to look for the corresponding parameters in the constructed table.

By utilizing the HSD parameter database 212, when a test slide is obtained for normalization, a titer level may be estimated for the test image using the procedures noted herein (see FIGS. 3B and 6). Once the titer level is estimated (weighted score for the test image) either before normalization or during normalization, the database of look-up values 212 may be referenced by the HSD transformation module 211 and statistical parameters corresponding to the estimated titer level of the query image may be retrieved and used for the alignment and scaling calculations as if they were the actual parameters specific for the query slide. Such standardized look-up values may be stored in a database 212 and accessed by system 200 on an as-needed basis. In some embodiments, the statistical parameters are used for both alignment and scaling.

Alignment of the Chromatic Distribution Coordinates

After the statistical parameters are derived or retrieved from database 212, alignment is performed (step 604). In general, the chromatic distribution coordinates ($c_x$, cy) for each pixel in each patch are matched to template chromatic distribution coordinates to provide aligned chromatic distribution coordinates ($c_x'$, cy'), using the derived or retrieved statistics.

As noted herein, $F(c_x, c_y)$ represents the chromatic distribution of the test image to be normalized. The process for normalization of the stain begins with translating the entire $F(c_x, c_y)$ distribution by subtraction of the mean of the $F(c_x, c_y)$ distribution and rotation along the major eigenvector of $\Sigma$, where $\Sigma$ denotes the covariance matrix of $F(c_x, c_y)$. Then, a piece-wise linear scaling is applied to match landmarks from the current distribution to those of the template slide. In the next step, the scaled distribution is rotated back along the derived angle to be aligned with the major eigenvector of the corresponding distribution in the template test image. The final step in the transformation of the involves translation of the distribution to the derived mean. In some embodiments, the output of alignment provides transformed chromatic distribution coordinates ($c_x'$, $c_y'$) for all pixels in all patches in the test image.

For the mean subtraction step: $(c_{x,c}, c_{y,c}) = (c_x, c_y) - (\mu_{x,i}, \mu_{y,i})$. Then we rotate the distribution along the major eigenvector of the ($c_x$, cy) distribution by multiplying by the unitary matrix $U_i$ from the singular value decomposition of the covariance matrix of the image under consideration $(c_{x,cr}, c_{y,cr}) = U_i^*(c_{x,c}, c_{y,c})$. In the third step we rotate again the distribution, this time along the major eigenvector of the template: $(c_{x,crr}, c_{y,crr}) = U_t^*(c_{x,cr}, c_{y,cr})$. Finally, we translate the whole distribution to match the mean of the template image: $(c_x', c_y') = (c_{x,crr}, c_{y,crr}) - (\mu_{x,t}, \mu_{y,t})$.

Density Scaling

After the statistical parameters are derived or retrieved from database 212, scaling is performed (step 605) using the derived or retrieved parameters. In general, the density distribution coordinates (D) for each pixel in each patch are matched to template density distribution coordinates to provide scaled chromatic distribution coordinates (D').

The density component (D) of the test image in the HSD color model is also transformed to match the density profile of the template image. In some embodiments, the distributions are normalized by matching the mean and standard deviation of the distribution to statistical parameters in the template image. The transformed density distribution is therefore determined by $$D' = \frac{D - \mu}{\deltaö} * \deltaö^{template} + \mu^{template}$$

where μ and ò are the weighted mean and the weighted standard deviation of the density distribution and $\deltaö^{template}$, $\mu^{template}$ are the corresponding values in the template, and where D and D' represent the densities before and after scaling, respectively.

Alternatively, the transformed density distribution may be determined by the following:

$$Dt = D - \mu + \mu_{template}$$

$$\mu_d = \text{mean}(Dt) \text{ (desired mean value)}$$

$$Ds = Dt / \sigma * \sigma\_t$$

$$\mu_o = \text{mean}(Ds) \text{ (obtained mean after normalizing the standard deviation)}$$

$$D' = Ds - \mu_o + \mu_d.$$

Weighting of the Transformed Coordinates

The final transformed coordinates in the HSD space will be the weighted sum of the original coordinates and the coordinates aligned and scaled with the stain class (e.g. hematoxylin) in the template. In this way, pixels that do not belong to the stain class, e.g. hematoxylin, will remain unchanged.

After the transformed chromatic distribution and density distribution coordinates (cx', cy', D') are obtained for each pixel in each patch (steps 604 and 605), the final transformed coordinates for each pixel are weighted by probability values, the probability values representing the probability that any particular pixel is a stain-class pixel (e.g. a hematoxylin pixel) (step 607). The probability values are derived by using a classifier (step 606), such as a Naïve-Bayes classifier, trained to determine the probability of a pixel being a stain-class pixel for each of the pixels in the test image. The training of the classifier is described further herein (see HSD classifier module).

The final coordinates ($c_{x,f}$, $c_{y,f}$, $D_f$), will be:

$$(c_{x,f}, c_{y,f}) = w_{stain}(c'_x, c'_y) + w_{no-stain}(c_x, c_y)$$

$$D_f = w_{stain} D' + w_{no-stain} D,$$

where $w_{stain}$ is the probability of a pixel belonging to the stain class and $w_{no-stain}$ is the probability of the pixel not belonging to this stain class.

Inverse Transformation Using the Weighted Transformation Coordinates

In a final step, the weight transformation coordinates are used to regenerate the test image in the RGB color space (step 607). This may be achieved by performing the reverse of the HSD transformation denoted herein.

Back transformation from ($c_x$, cy) to RGB may be performed using the following equations:

$$I_R = I \cdot (c_x + 1)$$

$$I_G = \frac{1}{2} \cdot I \cdot \left(2 - c_x + \sqrt{3} \cdot c_y\right),$$

where individual channel densities can be transformed back to RGB using the equation:

$$I_{ch} = I_{0,ch} \cdot e^{-D_{ch}}.$$

In some embodiments, for color alignment during RGB reconstruction, instead of employing the original hematoxylin color reference vector used for color deconvolution, the normalized average RGB OD vector from the pure hematoxylin pixels in the template image is used for reconstruction.

HSD Classifier Module

In some embodiments, a classifier is trained to recognize pixels in a template image that are stain pixels for the stain whose titer is being normalized from those that are not stain pixels, i.e. to provide a pixel classification result, where the derived HSD coordinates ($c_x$, cy, D) for each pixel in each patch from the HSD transform (step 603) are used as features.

In some embodiments, the classifier is trained to estimate which pixels are of a certain stain and which are not. This is achieved by considering a pixel to belong to a stain class, e.g. a hematoxylin class, if the following criteria are satisfied:

(a) the image is not white. An image is considered white if the overall optical density of the RGB image is lower than 0.2, and the optical densities from each of the RGB channels is less than 0.25. Derivation of optical densities is described herein.

(b) the Hue of the image is within the blue range. In some embodiments, the hue is obtained from the HSI (Hue Saturation Intensity) color decomposition. The hue is an angle defining the chromaticity of the image. For example, if the hue value is between 180 to 240 degrees, the resulting color is blue.

(c) there exist "cell-like" structures in the template image, that is the output of a DoG filter is higher than 0. DoG filters and their application to find "blobs" and cell-like structures is described herein.

After estimating the pixels that belong to the stain class, a Naïve-Bayes classifier is trained for the template image for hematoxylin versus non-hematoxylin pixels, using the HSD coordinates (cx, cy, D) as features. In some embodiments, the training set is obtained from the pixels selected from the FOVs/patches in the template image.

Other Components for Practicing Embodiments of the Present Disclosure

The system 200 of the present disclosure may be tied to a specimen processing apparatus that can perform one or more preparation processes on the tissue specimen. The preparation process can include, without limitation, deparaffinizing a specimen, conditioning a specimen (e.g., cell conditioning), staining a specimen, performing antigen retrieval, performing immunohistochemistry staining (including labeling) or other reactions, and/or performing in situ hybridization (e.g., SISH, FISH, etc.) staining (including labeling) or other reactions, as well as other processes for preparing specimens for microscopy, microanalyses, mass spectrometric methods, or other analytical methods.

The processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized using appropriate deparaffinizing fluid(s). After the paraffin is removed, any number of substances can be successively applied to the specimen. The substances can be for pretreatment (e.g., to reverse protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label or reporter molecule. Labels can include radioactive isotopes, enzyme substrates, co-factors, ligands, chemiluminescent or fluorescent agents, haptens, and enzymes.

The specimen processing apparatus can be an automated apparatus, such as the BENCHMARK XT instrument and SYMPHONY instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

After the specimens are processed, a user can transport specimen-bearing slides to the imaging apparatus. In some embodiments, the imaging apparatus is a brightfield imager slide scanner. One brightfield imager is the iScan Coreo brightfield scanner sold by Ventana Medical Systems, Inc. In automated embodiments, the imaging apparatus is a digital pathology device as disclosed in International Patent Application No.: PCT/US2010/002772 (Patent Publication No.: WO2011/049608) entitled IMAGING SYSTEM AND TECHNIQUES or disclosed in U.S. Patent Application No. 61/533,114, filed on Sep. 9, 2011, entitled IMAGING SYSTEMS, CASSETTES, AND METHODS OF USING THE SAME. International Patent Application No. PCT/US2010/002772 and U.S. Patent Application No. 61/533,114 are incorporated by reference in their entities.

The imaging system or apparatus may be a multispectral imaging (MSI) system or a fluorescent microscopy system. The imaging system used here is an MSI. MSI, generally, equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR).

An MSI system may include an optical imaging system, a portion of which contains a spectrally-selective system that is tunable to define a pre-determined number N of discrete optical bands. The optical system may be adapted to image a tissue sample, illuminated in transmission with a broad-band light source onto an optical detector. The optical imaging system, which in one embodiment may include a magnifying system such as, for example, a microscope, has a single optical axis generally spatially aligned with a single optical output of the optical system. The system forms a sequence of images of the tissue as the spectrally selective system is being adjusted or tuned (for example with a computer processor) such as to assure that images are acquired in different discrete spectral bands. The apparatus may additionally contain a display in which appears at least one visually perceivable image of the tissue from the sequence of acquired images. The spectrally-selective system may include an optically-dispersive element such as a diffractive grating, a collection of optical filters such as thin-film interference filters or any other system adapted to select, in response to either a user input or a command of the pre-programmed processor, a particular pass-band from the spectrum of light transmitted from the light source through the sample towards the detector.

An alternative implementation, a spectrally selective system defines several optical outputs corresponding to N discrete spectral bands. This type of system intakes the transmitted light output from the optical system and spatially redirects at least a portion of this light output along N spatially different optical paths in such a way as to image the sample in an identified spectral band onto a detector system along an optical path corresponding to this identified spectral band.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Any of the modules described herein may include logic that is executed by the processor(s). "Logic," as used herein, refers to any information having the form of instruction signals and/or data that may be applied to affect the operation of a processor. Software is an example of logic.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "programmed processor" encompasses all kinds of apparatus, devices, and machines for processing data, including by way of example a programmable microprocessor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., an LCD (liquid crystal display), LED (light emitting diode) display, or OLED (organic light emitting diode) display, for displaying information to the user and a keyboard and a pointing device, e.g., a mouse or a trackball, by which the user can provide input to the computer. In some implementations, a touch screen can be used to display information and receive input from a user. Other kinds of devices can be used to provide for interaction with a user as well; for example, feedback provided to the user can be in any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks). For example, the network 20 of FIG. 1 can include one or more local area networks.

The computing system can include any number of clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

EXAMPLES

Example 1—Imaging Algorithm Performance

To demonstrate the effectiveness of color normalization, we evaluated the performance of a cell detection algorithm in the images with and without normalization for different titer levels. The number of cells should be relatively constant along different titers, but if no normalization is applied, an increasing trend could be observed. FIGS. 8A and 8D show the variation with respect to titer 4 for 12 different slides (from 4 blocks) in the percentage of stained and non-stained cells with respect to the total number of cells. As shown, after a titer level of 4 there is an overestimation of the number of non-stained cells for the non-normalized images, but this problem was alleviated when the stain normalization was applied.

The performance of the proposed method was evaluated on a dataset consisting of 3020 whole slide images coming from 3 different scanners; for convenience, they are referred to as Scanner 1, Scanner 2 and Scanner 3. For each scanner, images for 3 different markers were collected, namely HER2, ER and Ki67. These images came from 12 blocks and there are 3 different sections available for each block. For each block and section, the results for titer levels 1 to 9 are provided. Also, some control whole slides are available for some of the markers/scanners. In Table 1 below, the number of whole slides are shown which were available for the different markers/scanners.

TABLE 1

Whole slide distribution.

|  | Scanner 1 | Scanner 2 | Scanner 3 |
|---|---|---|---|
| ER | 339 | 356 | 337 |
| HER2 | 324 | 322 | 317 |
| Ki67 | 347 | 340 | 338 |

For the titer level estimation, we show some results for Scanner 1 for each of the available markers using all the slides belonging to one block for testing and the rest for training. In Tables 2, 3 and 4 at the end of this Section we show the number of patches classified into each titer level for each slide as well as the final averaged class.

TABLE 2

Titer estimation results.

| | | HER2 | | |
|---|---|---|---|---|
| Section | | Sect 1 | Sect 2 | Sect 3 |
| Actual titer | Titer 1 | 2.32 | 2.92 | 2.05 |
| | Titer 2 | 3.67 | 3.18 | 2.93 |
| | Titer 3 | 4.19 | 3.77 | 3.34 |
| | Titer 4 | 5.04 | 4.95 | 4.43 |
| | Titer 5 | 4.65 | 5 | 4.55 |
| | Titer 6 | 5.83 | 5.20 | 4.93 |
| | Titer 7 | 6.09 | 5.41 | 6.05 |
| | Titer 8 | 7.26 | 6.98 | 7.09 |
| | Titer 9 | 8.46 | 7.74 | 8.50 |

Figure 8:
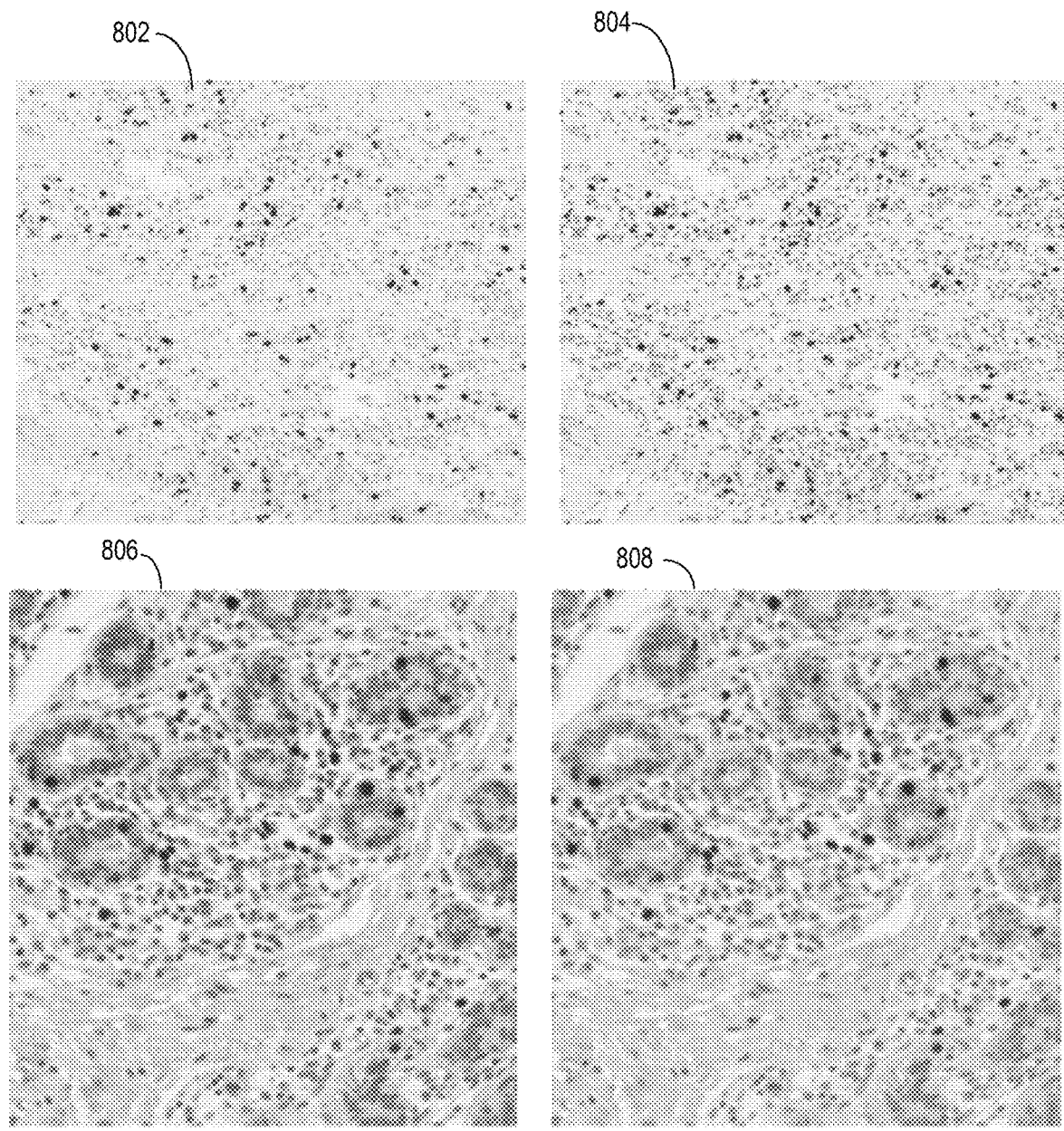
FIG. 8 illustrates a color normalization example.
Figure 9:
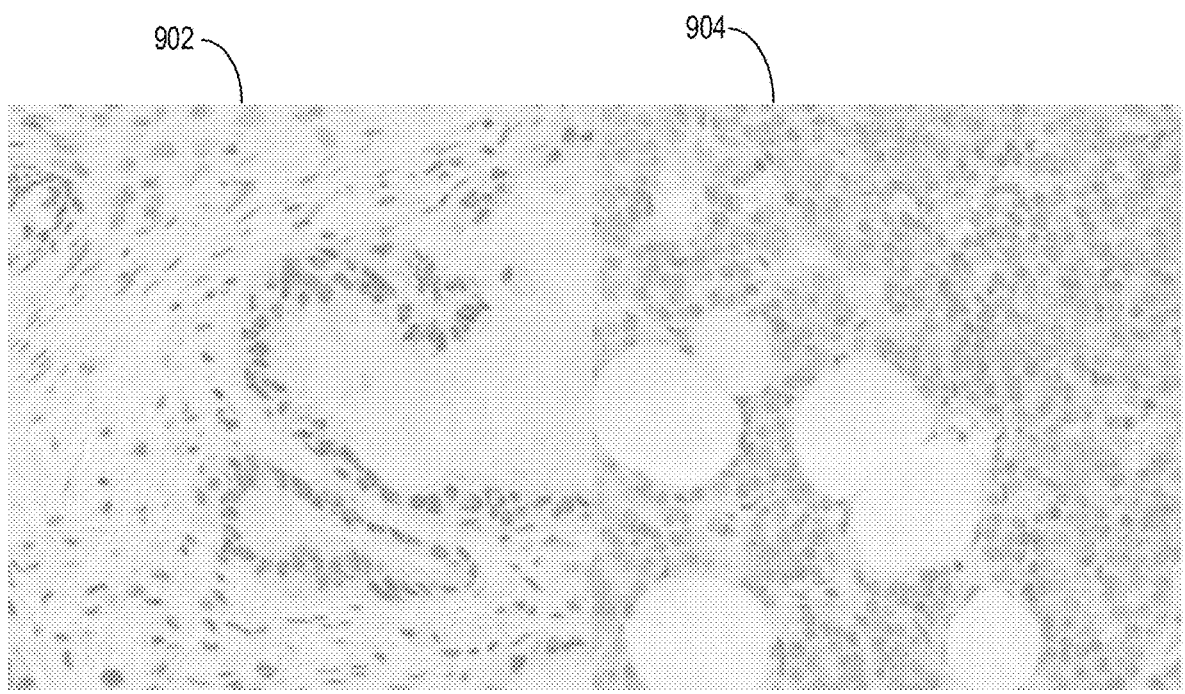
FIG. 9 illustrate FOVs with HER with a titer of 1 for a query dataset and a training set (see Table 2, herein).
Figure 10:
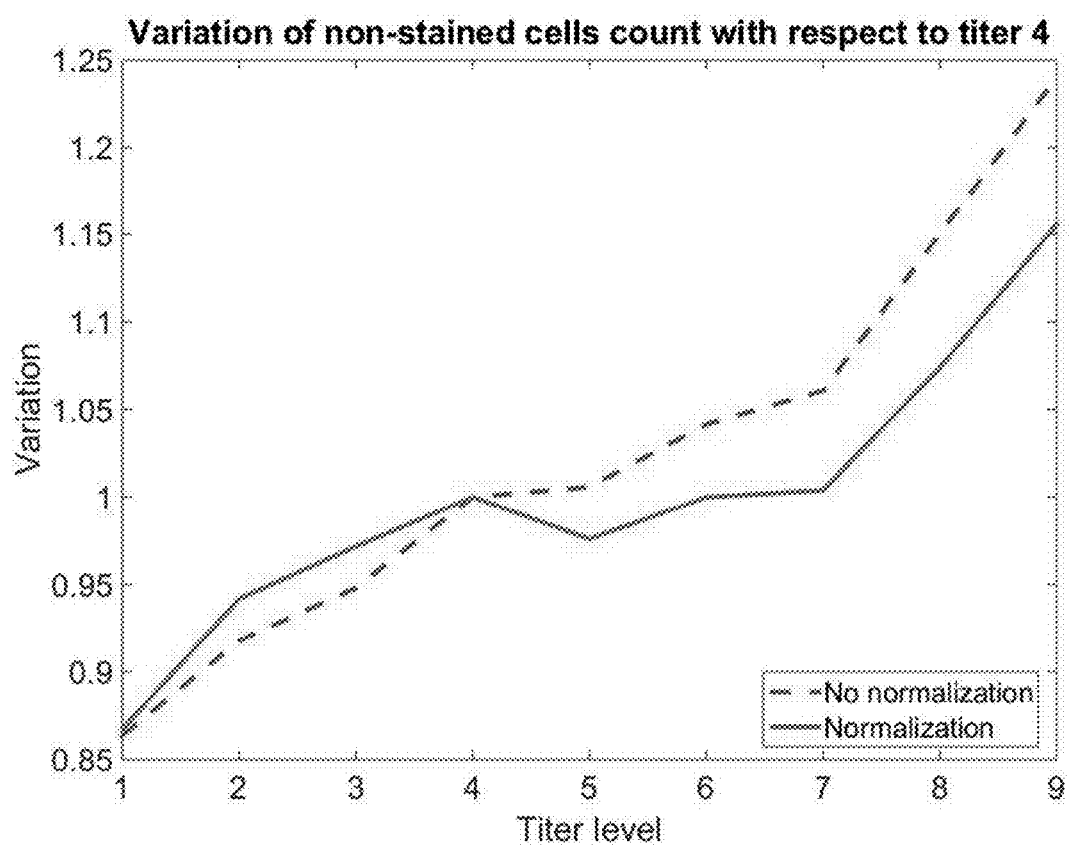
FIG. 10 illustrates average variation in the count of non-stained cells over three different blocks (81 whole slides images).

For the stain normalization part of the algorithm, we show some results in FIGS. 8 and 9 when normalizing a very faint and a very dark slide. Also, in FIG. 10 shows the performance of a cell detection algorithm in the images with and without stain normalization.

FIG. 8 illustrates a color normalization example, according to some embodiments. Image 802 shows show an example of an FOV from a slide with faint hematoxylin staining (titer 1) that has been normalized to a titer 4 template in image 804. It can be seen how the cells can be much easily identified in the image 804 due to the normalization algorithm. Similarly, image 806 shows an example FOV from a titer 9 slide, in which its correspondent normalized image to titer 4 is displayed in image 808.

Take for example HER2, it can be noted the overestimation for the lower titer levels. This is due to the difference in staining from block to block as can be seen in FIG. 9. For the block shown in Table 2 (Image 902) the hematoxylin staining is much darker than for the FOV in image 904 (belonging to another block in the training set). These results show again the need for normalization, as the specified titer can look different even for different blocks using same marker and scanner. Similar results can be observed for the other markers. In FIG. 9, the image 902 provides an example FOV with titer 1 from the block used to provide the results in Table 2. For this block, the titer was overestimated for the lower blocks. The image 904 shows an example FOV with the same titer. It can be seen that the hematoxylin level is much darker for the testing FOV than for the FOV used in training, leading to the reason for the overestimation and thus illustrating the need for normalization, given that even for the same marker and scanner, the intensity of the staining varies within different blocks.

Example 2—HSD Coordinates Alignment for Pure HTX Stain Pixels

HSD transform is performed on both the template and the target WSI, which converts the RGB optical density (OD) value to HSD coordinates (cx, cy, D). The first two coordinates contain the chromatic information which is independent of the amount of stain; while the last one is the density component which is linearly related to the stain concentration. The distribution of the (cx, cy) components in the target WSI is aligned to that in the template, and the density component is scaled to match the template. In our framework, instead of applying HSD coordinates alignment to all the stains, we adopt this alignment process for normalizing the pure HTX stain only. This is to maximally match the color and density distribution of HTX stain in the target image to that in the template image. The final normalized pure HTX pixels are obtained by transforming from HSD to RGB using the aligned HSD coordinates (cx', cy', D'). In our experiment, we found that histogram stretching for cx and cy, can lead to severe color artifacts when we try to align HTX stain whose hue-saturation distribution is drastically different from that of the template. Therefore, this step should be omitted for HTX normalization in IHC images.

Example 3—Special Handling of HTX Stain Mixture Pixels

When HTX stain is mixed with other stains, it is not feasible to derive the actual color and density distribution of the HTX stain in the mixture for HSD coordinates alignment. Therefore, we perform a "global" alignment to the average color and density of the pure HTX stain in the template image. In order to do that without altering the DAB stain in the mixture, we apply color deconvolution to both the template and the target image. Let $HTX_I$ ($DAB_I$) be the HTX (DAB) component from color deconvolution of the target image, and $HTX_T$ ($DAB_T$) be the HTX (DAB) component of the template image. For density alignment, we shift and scale $HTX_I$ to have the same mean and standard deviation as $HTX_T$, obtaining $HTX_f$. Then, RGB reconstruction is performed using $HTX_f$ and $DAB_I$. For color alignment during RGB reconstruction, instead of employing the original HTX color reference vector used for color deconvolution, we use the normalized average RGB OD vector from the pure HTX pixels in the template image for reconstruction. Background pixels and other non-HTX stain which does not co-localize with HTX remain unchanged without any normalization.

Example 4—Pure HTX Stain and HTX Stain Mixture Identification

Now we describe the method to identify pure HTX and HTX mixture pixels. Considering that a pixel could belong to the mixture of hematoxylin and eosin stain, a Naïve-Bayes classifier is trained to derive the probability of a pixel belonging to hematoxylin, eosin or background. Then the final transformed coordinates are the weighted sum of the stain specific transformed coordinates using the class probabilities as the weights. In our framework, only two classes, i.e., HTX and Non-HTX, are considered, this is to make it easy to generalize the approach to other type of stain that users want to normalize. The classifier is trained using the HSD coordinates of pixels from the template image. It is found in our experiment that classification error of this simple classifier may lead to undesired color artifacts if we use the classification probability as the weight as is, especially for class boundary pixels. Therefore, we only apply the weighting scheme to the pure HTX pixels which are defined using the following criteria:

The pixel is not white, i.e., the overall OD is <0.2 and the OD from at least one of the RGB channels is >0.25.

The Hue of the pixel is within a pre-defined blue range in the HSD space.

There are some "cell-like" structures, i.e., output of a DoG filter applied on the unmixed HTX component is >0.

To identify the HTX mixture pixel, a DoG filer is applied to the unmixed DAB component. A pixel is determined to be HTX mixture if the DOG filter output is >0, both of the pixel's unmixed DAB and HTX component are higher than a fixed threshold (th=0.2), and the pixel's hue is outside the pre-defined blue range. Other pixels remain unchanged.

Example 5—Whole Slide Normalization

Figure 12:
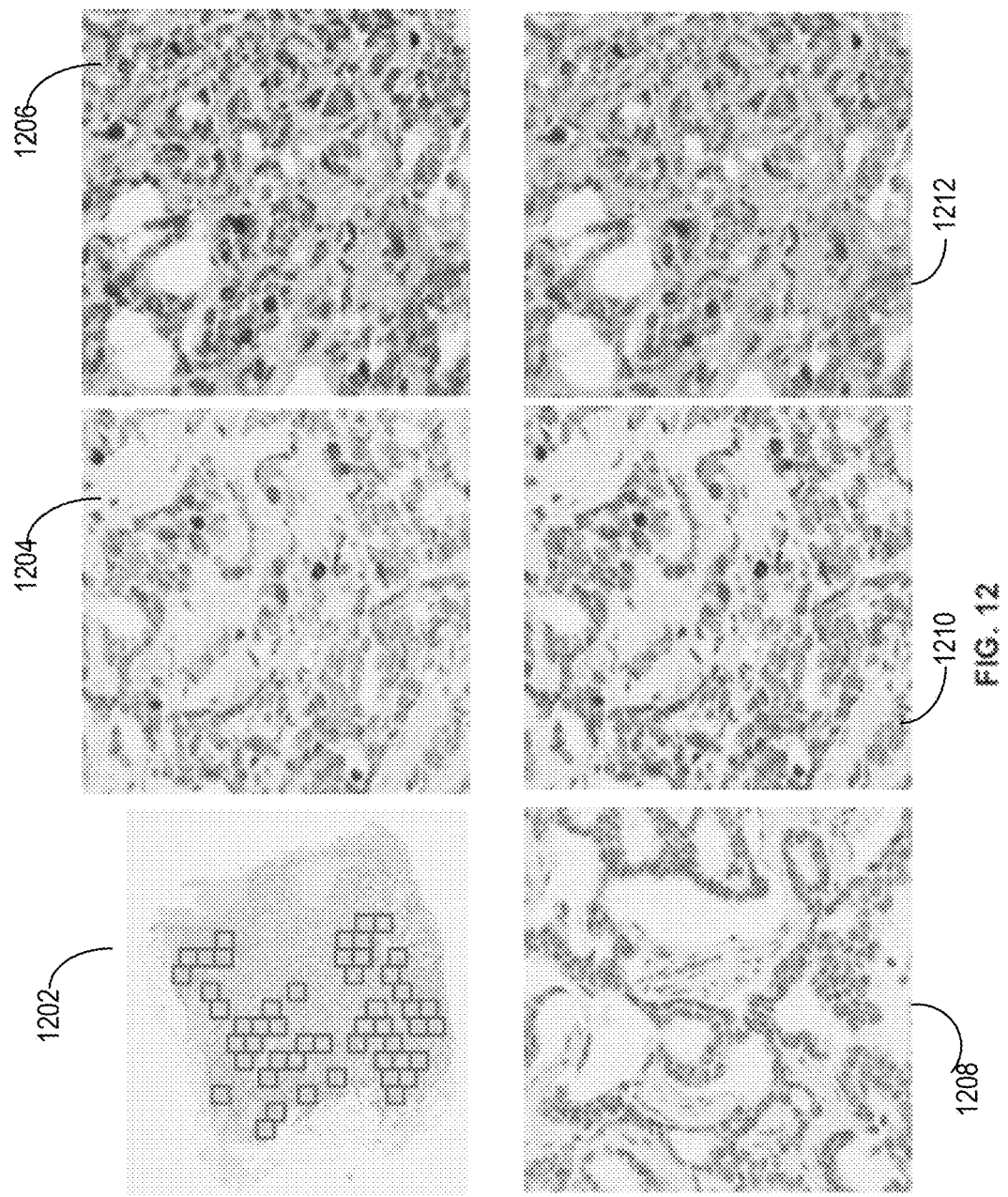
FIG. 12 illustrates an example of selected FOVs in a WSI.

Note that the number of pixels in a WSI is very large. Thus, using all the pixels in the WSI to solve the statistics needed for normalization is computationally very expensive and unnecessary. Instead, we design a general method to select pixels that are representative for the HTX stain in the WSI. In our implementation, the top 50 field of view (FOV) images (600×600 pixels), whose mean unmixed HTX component is closest to 80th percentile among all the FOVs in the WSI, are first selected. FIG. 12 shows an example of the selected FOVs. In FIG. 12, image 1202 shows an example of selected FOVs in a WSI. Image 1204 shows a sample FOV from a titer 1 slide. Image 1206 shows a sample FOV from a tier 9 slide. Image 1208 shows a sample FOV from the template slide. Image 1210 shows a normalized sample FOV from titer 1 slide. Image 1212 shows a normalized sample FOV from titer 9 slide. Afterwards, we further select the patches (100×100 pixels) from each FOV which contain a good amount of HTX stain. This is achieved by discarding the patches which contains mostly (>70%) background pixels. After patch selection, we identify the pure HTX pixels using the criteria described in Example 4. These pixels will be used to solve all the statistics in the Examples above. This step, a pixel is considered as background if its OD is lower than the 25th percentile of all the blue pixels in that FOV, where the blue pixels are identified as those whose hue is in a pre-defined blue range in the HSD space.

Example 6—Results

We evaluate the performance of the proposed method on a dataset consisting of 324 HER2 stained IHC WSI. These slides are from 12 breast cancer tissue blocks and 27 slides are cut out from each block. The slides from the same block are stained using HTX at nine controlled concentration levels, which are represented by a titer number valued from 1 to 9, where 1 indicating the lightest staining and 9 the darkest. Each HTX titer is applied to a group of 3 consecutive slides. We select a WSI from titer 4 as the template image.

To evaluate the performance of the presented method qualitatively, we show in FIG. 11 two example FOVs from slides with HTX concentration level titer 1 and titer 9, respectively. The HTX stains in the normalized FOV images are visually more consistent across different concentration levels, while the DAB stain remains unchanged from the original slide.

Figure 13:
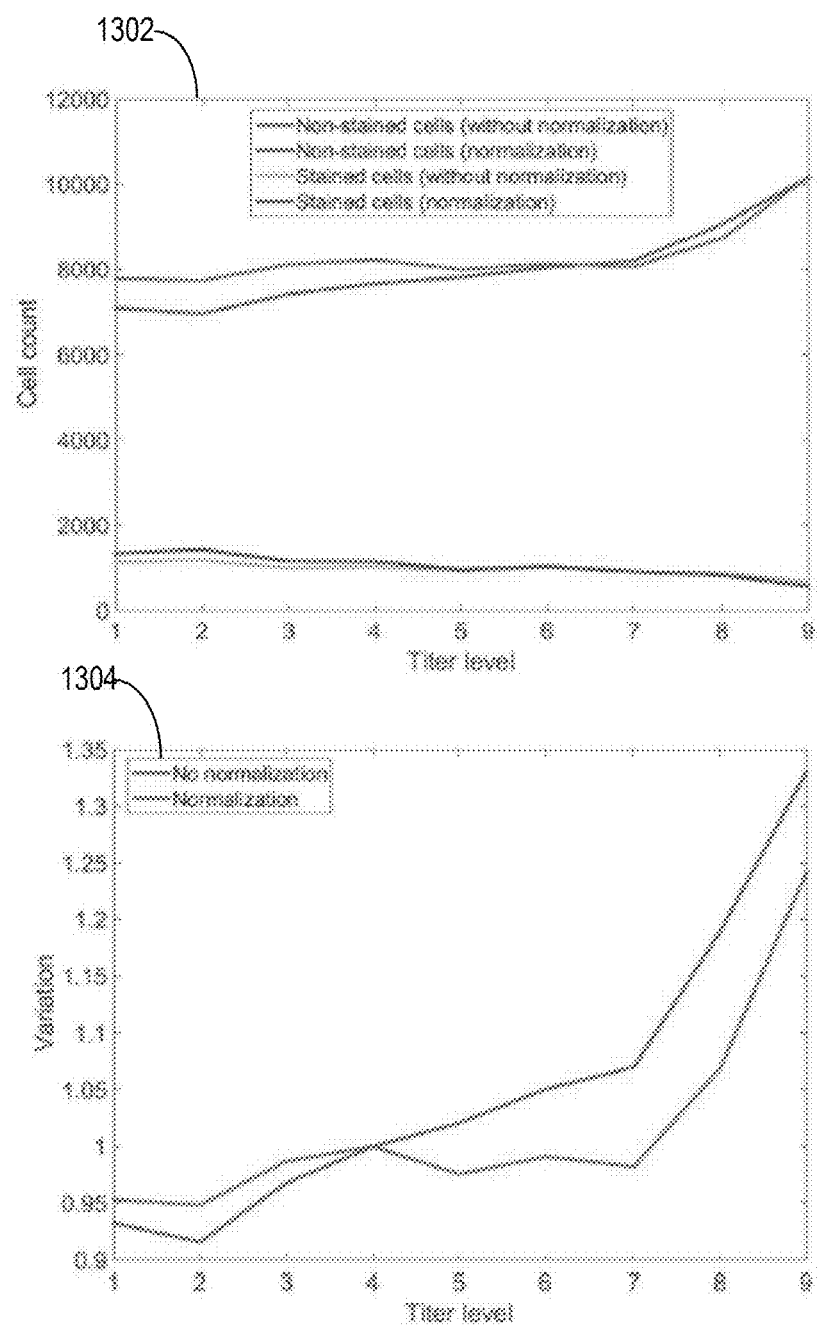
FIG. 13 provides a comparison of HER2 tumor cell detection algorithm output before and after stain normalization.

To evaluate the impact of the presented method on image analysis algorithm, an in-house off-the-shelf HER2 tumor cell detection algorithm is applied on the 324 slides. Specifically, multiple FOVs from each slide are processed to generate the cell count readout for the slide and these FOVs are registered cross the slides from the same tissue block. FIG. 13 shows a comparison between: (i) an image 1302 that is associated HER2 tumor cell detection algorithm output before stain normalization; and (ii) and image 1304 that is associated HER2 tumor cell detection algorithm output after stain normalization. In general, before normalization, the non-stained (blue) cell count has clear dependency on the HTX concentration level; after normalization, such dependency is much reduced. For the stained (brown) cells, the dependency is both small before and after normalization. To further illustrate the algorithm output consistency cross different HTX concentration levels, the average non-stained cell count for each titer is normalized with respect to the same readout generated by the titer 4 slides from the same tissue block. If the output consistency is good, this number should remain more or less constant from titer to titer and close to value 1 (=1 for titer 4). FIG. 12 clearly shows the consistency improvement cross all the titers. It is also observed that titer 9 slides still generate significantly higher cell count than titer 4 slides even after normalization. We found that this is because extremely high concentration HTX leads to severe background staining, which cause the algorithm to yield a lot of false cell detection in the background, which cannot be resolved through stain normalization only.

Applicants therefore submit that HTX stain variation pose challenges for IHC image analysis. We present a framework for single stain normalization which can normalize the HTX stain by aligning the chromatic and density distribution to a template image in the HSD color space. Normalizing HTX in stain mixture is handled through aligning unmixed HTX component's mean and standard deviation, and using the average RGB OD vector of the pure HTX pixels in the template image as the HTX reference color vector during RGB reconstruction. Experiment results show that the proposed method improves the HTX stain consistency cross different images without affecting the DAB stain; and significantly reduces the dependency of image analysis algorithm on the HTX stain variation. The method can be extended to other IHC stains and will be the future work.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

Further disclosed herein is a method of assaying a titer of a first stain within a whole slide image of a biological sample stained with one or more stains, and normalizing the whole slide image relative to the titer of the first stain comprising:

computing a weighted average titer score for the whole slide image based on derived first stain image features, and normalizing the whole slide image to a template image if the computed weighted average score is not within a predefined titer range, wherein the whole slide image is normalized by (a) matching whole slide image chromatic and density distributions to template image chromatic and density distributions, wherein the chromatic and density distributions of both the whole slide and template images are derived within a color model that incorporates density information, and (b) reconstructing an RGB image by inversing transforming the whole slide image within the color model incorporating the density information using weighted transformation coordinates.

Further disclosed is a method, wherein the weighted average titer score is computed by (a) deriving a plurality of first stain image features from each of a series of image patches in the whole slide image, and (b) classifying the plurality of derived image features from each of the image patches using a trained feature-identification classifier.

Further disclosed is a method, wherein the series of image patches are derived by (a) extracting a predefined number of FOVs from the whole slide image; (b) computing a set of patches for each of the extracted FOVs; and (c) retaining those patches from the set of patches for each extracted FOV that meet threshold patch criteria.

Further disclosed is a method, wherein the first stain image features are stain color features and stain intensity features.

Further disclosed is a method, wherein the whole slide image chromatic and density distributions are matched to the template image chromatic and density distributions by (i) performing a transform within the image patches of the whole slide image to obtain chromatic and density distribution coordinates (cx, cy, D) for all pixels in each of the image patches; (ii) shifting and rotating the obtained chromatic distribution coordinates (cx, cy) in the whole slide image to have a same mean and orientation as template chromatic coordinates to provide aligned chromatic coordinates (cx', cy') for each pixel in each image patch; and (iii) scaling the obtained density distributions (D) from the whole slide image to have a same weighted mean and weighted standard deviation as template density distributions to provide scaled density distributions (D') for each pixel in each image patch.

Further disclosed is a method, wherein the weighted transformation coordinates are derived by (i) computing probabilities that pixels in the image patches are first stain pixels; and (ii) weighting the aligned chromatic density distribution coordinates and scaled density distribution coordinates (cx', cy', D') with the computed probabilities.

Further disclosed is a method, wherein the matching of the obtained chromatic and density distributions to the template image chromatic and density distributions utilize predetermined statistical parameters, wherein the predetermined statistical parameters chosen are particular for a titer level that approximates the weighted average titer score for the whole slide image.

Further disclosed is a method, wherein the first stain is hematoxylin.

Further disclosed is a method, wherein the predefined titer range is between 4 and 6.

Further disclosed is a method, wherein the color module that incorporates density information is an HSD color module.

Further disclosed is an imaging system for normalizing a titer of a first stain within a query image to a titer of the first stain in a template image, the query image being of a biological sample stained with at least the first stain, the imaging system comprising: (i) one or more processors, and (ii) a memory coupled to the processor, the memory to store computer-executable instructions that, when executed by the one or more processors, cause the one or more processors to perform operations comprising:

deriving chromatic and density distribution coordinates for each pixel in generated patches within the query image, the deriving performed within a color module that incorporates density information;

transforming the derived chromatic and density distribution coordinates for each pixel in the generated patches using predetermined alignment and scaling parameter values specific for an estimated titer level of the query image to provide transformed chromatic and density distribution coordinates for each pixel in the generated patches; and reconstructing an RGB image by inversely transforming the query image within the color model that incorporates the density information using the transformed chromatic and density distribution coordinates weighted by pixel probability values.

Further disclosed is an imaging system, wherein the imaging system further comprises a staining apparatus.

Further disclosed is an imaging system, wherein the biological sample is stained with at least two stains.

Further disclosed is an imaging system, wherein the transforming of the derived chromatic and density distribution coordinates for each pixel in the generated patches comprises (a) shifting and rotating the derived chromatic distribution coordinates (cx, cy) for each pixel in the generated patches to have a same mean and orientation as template chromatic coordinates to provide transformed chromatic coordinates (cx', cy') for each pixel in the generated patches; and (b) scaling the obtained density distributions (D) for each pixel in the generated patches to have a same weighted mean and weighted standard deviation as template density distributions to provide transformed density distributions (D') for each pixel the generated patches.

Further disclosed is an imaging system, wherein the alignment and scaling parameter values specific for the first stain at a plurality of titer levels are stored in the memory.

Further disclosed is an imaging system, wherein the estimated titer level of the query image is determined by computing a weighted average titer score for the query image based on derived first stain color and intensity features, and wherein the alignment and scaling parameters selected approximate the weighted average titer score of the query image.

Further disclosed is an imaging system, wherein the weighted average score is computed by (a) deriving a plurality of first stain image features from the generated patches in the query image, and (b) classifying the plurality of derived image features from each of the generated patches using a trained titer-identification classifier.

Further disclosed is an imaging system, wherein the titer-identification classifier is a multi-class classifier trained on first stain color and intensity features derived from standardized samples using first stain titer levels as class labels.

Further disclosed is an imaging system, wherein the patches are generated by (a) extracting a predefined number of FOVs from the query image; (b) generating a set of patches for each of the extracted FOVs; and (c) retaining those patches from the set of patches for each extracted FOV that meet threshold patch criteria.

Further disclosed is an imaging system, wherein the weighted transformed chromatic and density distribution coordinates are derived by (i) computing probabilities that pixels are first stain pixels; and (ii) weighting the transformed chromatic and density distribution coordinates with the computed probabilities.

Further disclosed is an imaging system, wherein the color module that incorporates density information is an HSD color module.

Further disclosed is a non-transitory computer-readable medium for assaying a titer of a first stain within a whole slide image of a biological sample stained with one or more stains, and normalizing the whole slide image relative to the titer of the first stain comprising:
  computing a weighted average titer score for the whole slide image based on derived first stain image features, and
  normalizing the titer of the first stain whole slide image to a template image first stain titer, wherein the whole slide image is normalized by:
  deriving chromatic and density distribution coordinates in the query image within a color module that incorporates density information;
  aligning the derived chromatic distributions coordinates in the query image with template image chromatic distribution coordinates to provide transformed chromatic distribution coordinates, wherein the alignment comprises shifting and rotating the derived chromatic distribution coordinates in the query image to have a same mean and orientation as template chromatic distribution coordinates, wherein the step of alignment utilizes predetermined alignment parameters matched to the computed weighted average titer score of the whole slide image;
  scaling the derived density distribution coordinates in the query image with template image density distribution coordinates to provide transformed density distribution coordinates, wherein the scaling comprises transforming the derived density distribution coordinates to have the same weighted mean and weighted standard deviation as template density distribution coordinates, wherein the step of scaling utilizes predetermined scaling parameters matched to the computed weighted average titer score of the whole slide image; and
  reconstructing an RGB image by inversely transforming the query image within the color model incorporating the density information using weighted transformed chromatic and density distribution coordinates.

Further disclosed is a non-transitory computer-readable medium, wherein the first stain in the whole slide image is normalized to the template image first stain titer if the computed weighted average titer score falls outside a predetermined threshold titer score range.

Further disclosed is a non-transitory computer-readable medium, wherein the predetermined threshold titer score ranges from about 3 to about 6.

Further disclosed is a non-transitory computer-readable medium, wherein the weighted average titer score for the whole slide image based on derived first stain image features is computed by (a) extracting a predefined number of FOVs from the whole slide image; (b) computing a set of patches within each of the extracted FOVs; (c) deriving a plurality of first stain color and intensity features from each patch within the set of patches; (d) classifying the plurality of derived first stain color and intensity features using a trained titer-classifier; and (e) computing a weighted average scored based on the classification results from all of the patches.

Further disclosed is a non-transitory computer-readable medium, wherein the color module that incorporates density information is an HSD color module.

What is claimed is:

1. A method comprising:
  determining an estimated titer level of a query image, the query image being an image of a biological sample stained with a stain, wherein the estimated titer level of the query image is determined in-part by classifying stain image features derived from image patches of the query image; and
  normalizing a titer level of the query image, wherein the titer level of the query image is normalized by:
    deriving chromatic distribution coordinates and density distribution coordinates in the query image within a color model which incorporates density information;
    aligning, based in-part on a first parameter value associated with the estimated titer level of the query image, the chromatic distributions coordinates in the query image with template image chromatic distribution coordinates to provide transformed chromatic distribution coordinates;
    scaling, based in-part on a second parameter value associated with the estimate titer level of the query image, the density distribution coordinates in the query image with template image density distribution coordinates to provide transformed density distribution coordinates; and
    reconstructing an RGB image by inversely transforming the query image within the color model incorporating the density information using weighted transformed chromatic distribution coordinates and weighted transformed density distribution coordinates.

2. The method of claim 1, wherein the image patches are derived by:
  extracting a predefined number of FOVs from the query image;
  computing a set of patches for each FOV of the FOVs; and
  retaining those patches from the set of patches for each FOV of the FOVs that meet threshold patch criteria.

3. The method of claim 1, wherein the determining the estimated titer level of the query image occurs prior to the normalizing the titer level of the query image.

4. The method of claim 1, wherein the determining the estimated titer level of the query image occurs during the normalizing the titer level of the query image.

5. The method of claim 1, wherein the weighted transformed chromatic distribution coordinates and the weighted transformed density distribution coordinates are derived by:

computing probabilities that pixels are stain pixels; and
weighting the transformed chromatic distribution coordinates and the transformed density distribution coordinates with the probabilities.

6. The method of claim 1, wherein aligning the chromatic distributions coordinates comprises shifting and rotating the chromatic distribution coordinates in the query image to have a same mean and orientation as the template image chromatic distribution coordinates.

7. The method of claim 1, wherein the scaling the density distribution coordinates comprises transforming the density distribution coordinates to have a same weighted mean and weighted standard deviation as the template image density distribution coordinates.

8. A system comprising:
one or more processors; and
one or more memories coupled to the one or more processors, the one or more memories to store computer-executable instructions that, when executed by the one or more processors, cause the system to perform operations comprising:
determining an estimated titer level of a query image, the query image being an image of a biological sample stained with a stain, wherein the estimated titer level of the query image is determined in-part by classifying stain image features derived from image patches of the query image; and
normalizing a titer level of the query image, wherein the titer level of the query image is normalized by:
deriving chromatic distribution coordinates and density distribution coordinates in the query image within a color model which incorporates density information;
aligning, based in-part on a first parameter value associated with the estimated titer level of the query image, the chromatic distributions coordinates in the query image with template image chromatic distribution coordinates to provide transformed chromatic distribution coordinates;
scaling, based in-part on a second parameter value associated with the estimate titer level of the query image, the density distribution coordinates in the query image with template image density distribution coordinates to provide transformed density distribution coordinates; and
reconstructing an RGB image by inversely transforming the query image within the color model incorporating the density information using weighted transformed chromatic distribution coordinates and weighted transformed density distribution coordinates.

9. The system of claim 8, wherein the image patches are derived by:
extracting a predefined number of FOVs from the query image;
computing a set of patches for each FOV of the FOVs; and
retaining those patches from the set of patches for each FOV of the FOVs that meet threshold patch criteria.

10. The system of claim 8, wherein the determining the estimated titer level of the query image occurs prior to the normalizing the titer level of the query image.

11. The system of claim 8, wherein the determining the estimated titer level of the query image occurs during the normalizing the titer level of the query image.

12. The system of claim 8, wherein the weighted transformed chromatic distribution coordinates and the weighted transformed density distribution coordinates are derived by:
computing probabilities that pixels are stain pixels; and
weighting the transformed chromatic distribution coordinates and the transformed density distribution coordinates with the probabilities.

13. The system of claim 8, wherein aligning the chromatic distributions coordinates comprises shifting and rotating the chromatic distribution coordinates in the query image to have a same mean and orientation as the template image chromatic distribution coordinates.

14. The system of claim 8, wherein the scaling the density distribution coordinates comprises transforming the density distribution coordinates to have a same weighted mean and weighted standard deviation as the template image density distribution coordinates.

15. A non-transitory computer-readable medium storing instructions which, when executed by one or more processors, cause a system to perform operations comprising:
determining an estimated titer level of a query image, the query image being an image of a biological sample stained with a stain, wherein the estimated titer level of the query image is determined in-part by classifying stain image features derived from image patches of the query image; and
normalizing a titer level of the query image, wherein the titer level of the query image is normalized by:
deriving chromatic distribution coordinates and density distribution coordinates in the query image within a color model which incorporates density information;
aligning, based in-part on a first parameter value associated with the estimated titer level of the query image, the chromatic distributions coordinates in the query image with template image chromatic distribution coordinates to provide transformed chromatic distribution coordinates;
scaling, based in-part on a second parameter value associated with the estimate titer level of the query image, the density distribution coordinates in the query image with template image density distribution coordinates to provide transformed density distribution coordinates; and
reconstructing an RGB image by inversely transforming the query image within the color model incorporating the density information using weighted transformed chromatic distribution coordinates and weighted transformed density distribution coordinates.

16. The non-transitory computer-readable medium of claim 15, wherein the image patches are derived by:
extracting a predefined number of FOVs from the query image;
computing a set of patches for each FOV of the FOVs; and
retaining those patches from the set of patches for each FOV of the FOVs that meet threshold patch criteria.

17. The non-transitory computer-readable medium of claim 15, wherein the determining the estimated titer level of the query image occurs prior to the normalizing the titer level of the query image.

18. The non-transitory computer-readable medium of claim 15, wherein the determining the estimated titer level of the query image occurs during the normalizing the titer level of the query image.

19. The non-transitory computer-readable medium of claim 15, wherein the weighted transformed chromatic distribution coordinates and the weighted transformed density distribution coordinates are derived by:

computing probabilities that pixels are stain pixels; and
weighting the transformed chromatic distribution coordinates and the transformed density distribution coordinates with the probabilities.

20. The non-transitory computer-readable medium of claim 15, wherein aligning the chromatic distributions coordinates comprises shifting and rotating the chromatic distribution coordinates in the query image to have a same mean and orientation as the template image chromatic distribution coordinates, and wherein the scaling the density distribution coordinates comprises transforming the density distribution coordinates to have a same weighted mean and weighted standard deviation as the template image density distribution coordinates.

\* \* \* \* \*